United States Patent
Winter et al.

(10) Patent No.: US 6,613,797 B2
(45) Date of Patent: Sep. 2, 2003

(54) XANTHONE ANALOGS FOR TREATING INFECTIOUS DISEASES AND COMPLEXATION OF HEME AND PORPHYRINS

(75) Inventors: Rolf W. Winter, Portland, OR (US); Michael K. Riscoe, Tualatin, OR (US); David J. Hinrichs, Lake Oswego, OR (US)

(73) Assignee: Interlab, Inc., Lake Oswego, OR (US)

( * ) Notice: Subject to any disclaimer, the term of this patent is extended or adjusted under 35 U.S.C. 154(b) by 0 days.

(21) Appl. No.: 09/728,051

(22) Filed: Dec. 1, 2000

(65) Prior Publication Data

US 2002/0055644 A1 May 9, 2002

Related U.S. Application Data

(60) Provisional application No. 60/168,784, filed on Dec. 2, 1999.

(51) Int. Cl.⁷ .................... A61K 31/352; A61K 31/382; C07D 311/82; C07D 335/12
(52) U.S. Cl. .................. 514/437; 514/455; 549/27; 549/280; 549/391
(58) Field of Search ................... 549/27, 28 D, 549/391; 514/437, 455

(56) References Cited

U.S. PATENT DOCUMENTS

| | | |
|---|---|---|
| 3,050,440 A | 8/1962 | Richter |
| 3,346,579 A | 10/1967 | Sheehan et al. |
| 3,639,612 A | 2/1972 | De Long et al. |
| 3,714,194 A | 1/1973 | Ulrich |
| 3,755,593 A | 8/1973 | Adams et al. |
| 3,829,578 A | 8/1974 | Fleming et al. |
| 3,887,574 A | 6/1975 | Ellis et al. |
| 3,947,594 A | 3/1976 | Randall |
| 3,948,920 A | 4/1976 | Nabih |
| 3,953,602 A | 4/1976 | Shemano |
| 3,957,986 A | 5/1976 | Carr et al. |
| 3,985,783 A | 10/1976 | Johnson et al. |
| 4,015,017 A | 3/1977 | Gazave et al. |
| 4,284,627 A | 8/1981 | Raether et al. |
| 4,290,954 A | 9/1981 | Onogi et al. |
| 4,311,710 A | 1/1982 | Clinton et al. |
| 4,335,046 A | 6/1982 | Horner |
| 4,539,412 A | 9/1985 | Archer |
| 4,585,876 A | 4/1986 | Fischer et al. |
| 4,661,607 A | 4/1987 | Koga et al. |
| 4,670,265 A | 6/1987 | Sydiskis et al. |
| 4,816,479 A | 3/1989 | Koga et al. |
| 4,996,230 A | 2/1991 | Gapinski |
| 5,070,085 A | 12/1991 | Markham |
| 5,093,372 A | 3/1992 | Uedo et al. |
| 5,281,620 A | 1/1994 | Denny et al. |
| 5,977,077 A | 11/1999 | Winter et al. |

FOREIGN PATENT DOCUMENTS

| JP | 10203976 | * 8/1998 |
|---|---|---|
| WO | 97/34482 | * 9/1997 |

OTHER PUBLICATIONS

Bentue–Ferrer et al., "Comparative Evaluation of Scavenger Properties of Exifone, Piracetam and Vinburnine," Laboratory of Clinical and Experimental Pharmacology, pp. 323–328 (1988).

Descombe et al., "Determination of Exifone in Human Plasma and Urine by High–Performance Liquid Chromatography with Electro–Chemical Detection," *J. Chromatogr.* 496:345–353(1989).

Hafuri et al., "Mechanism of Inhibition of Reverse Transcriptase by Quinone Antibiotics–II. Dependence of Putative Quinone Pocket on the Emzyme Molecule," *J. Antibiotics XLI*: 1471–1478 (1988).

Porsolt et al., "Antagonism by Exifone, a New Cognitive Enhancing Agent, of the Amnesias Induced by Four Benzo–diazepines in Mice," *Psychopharmacology* 95:291–297 (1988).

Vennerstrom and Eaton, "Oxidants, Oxidant Drugs, and Malaria," *J. Med. Chem.* 31:1269–1277(1988).

Denjean et al., "Nouveautés en Hépatotoxicité Médicamenteuse," *Ann. Gastroentérol. Hépatol.* 26:293–298 (1990).

Larrey et al., "Hépatites probablement dues à l'exifone (Adlone®)," *Gastroenterol Clin. Biol.* 13:397–400 (1989).

Ouzan et al., "Atteintes hépatiques aiguës graves a l'exifone," *Therapie* 45:436–437 (1990).

Ghosal et al., "Chemical Constituents of Gentianaceae XXIV: Anti–*Mycobacterium tuberculosis* Activity of Naturally Occuring Xanthones and Synthetic Analogs," *J. Pharm. Sci.* 67:(721–722 (1978).

Hambloch and Frahm, "QSAR with the Tuberculostatic Activity of Polyhydroxy Xanthones and Their 13C—NMR Chemicals Shifts," *Eur. J. Med. Chem.* 20:71–77 (1985).

Hostettmann et al., Strategy in the Search for New Biologically Active Plant Constituents, Proceedings of the Phytochemical Society of Europe, V. 37, Phytochemistry of Plants Used in Traditional Medicine, K. Hostettmann, A. Marston, M. Maillard, and M. Hamburger(eds). Oxford Science Publishers (1995).

(List continued on next page.)

*Primary Examiner*— Taofiq Solola
(74) *Attorney, Agent, or Firm*—Klarquist Sparkman, LLP

(57) ABSTRACT

Therapeutic compounds and compositions for the treatment of infectious diseases are disclosed. The compounds are xanthones and xanthone derivatives, such as 3,5-bis-ε-(N,N-diethylamino)amyloxyxanthone. The described compositions include such compounds and a pharmaceutical carrier. These compositions also can include additional materials conventionally used to form therapeutic compositions. 3,5-bis-ε-(N,N-diethylamino)amyloxyxanthone has an $IC_{50}$ for *Plasmodium falciparum* of about 0.15 μM, and an $IC_{50}$ for *Leishmania mexicana* of <<0.5 μM. These compositions are additionally useful for forming soluble complexes with heme and porphyrins.

29 Claims, 7 Drawing Sheets

OTHER PUBLICATIONS

Sultanbawa, "Tetrahedron Report Number 84—Xanthonoids of Tropical Plants," *Tetrahedron* 36:1465–1506 (1980).

Wang et al., "Swertifrancheside, and HIV—Reverse Transcriptase Inhibitor and the First Flavone—Xanthone Dimer, from *Swertia franchetianna*," *J. Nat. Prod.* 57:211–217 (1994).

The Merck Index, Tenth Edition, p. 689, (entry 4656) 1983).

Gaekwad et al., "Caplus Abstract," *An 1979:121350* (1979).

Kurduker et al., "Chemical Abstracts," *The American Chemical Society 59:8*, 8689 (1963).

Shanaranarayan et al., "Caplus Abstract," *AN 1980:352* (1980).

Ignatuschenko et al., Xanthones as Antimalarial Agents; Studies of a Possible Mode of Action,: *Federation of European Biochemical Societies 409*:67–73 (1997).

Arky et al., "Physicians' Desk Reference®," *Medical Economics Company, Inc., PDR* 51 1206–1207 Edition (1997).

Mendiratta et al, "Erythrocyte Defenses Against Hydrogen Peroxide: The Role of Ascorbic Acid," *Biochimica et Biophysica Acta 1380*:389–395 (1998).

Srivastava et al., "Atovaquone, a Broad Spectrum Antiparasitic Drug, Collapses Mitochondrial Membrane Potential in a Malarial Parasite," *The Journal of Biological Chemistry 272:7* 3961–3966 (1997).

Winter et al., "Potentiation of a Antimalarial Oxidant Drug," *Antimicrobial Agents and Chemotherapy* 1449–1454 (1997).

Undenfriend et al., "Ascorbic Acid in Aromatic Hydroxylation: I. A Model System for Aromatic Hydroxylation," 731–739 (1953).

Chrastil et al., "Contribution of Cytochromes and Proteins to the Effect of Ascorbic Acid on Artificial and Microsomal Hydroxylation Systems Containing Oxygen and Hydrogen Peroxide,"*Biochem. J. 170*:693–698 (1978).

Marva et al., The Effects of Ascorbate–Induced Free Radicals on Plasmodium Falciparum, *Trop. Med. Parasitol. 43*:17–23 (1992).

Aust et al., Role of Metals in Oxygen Radical Reactions, *Journal of Free Radicals in Biology & Medicine 1*:3–25 (1985).

Roginsky et al., "Ascorbyl Radical As Natural Indicator of Oxidative Stress: Quantitative Regularities," *Free Radical Biology & Medicine 17:2* 93–103 (1994).

\* cited by examiner

Entry into acidic digestive vacuole (pH 4.8 to 5.5)

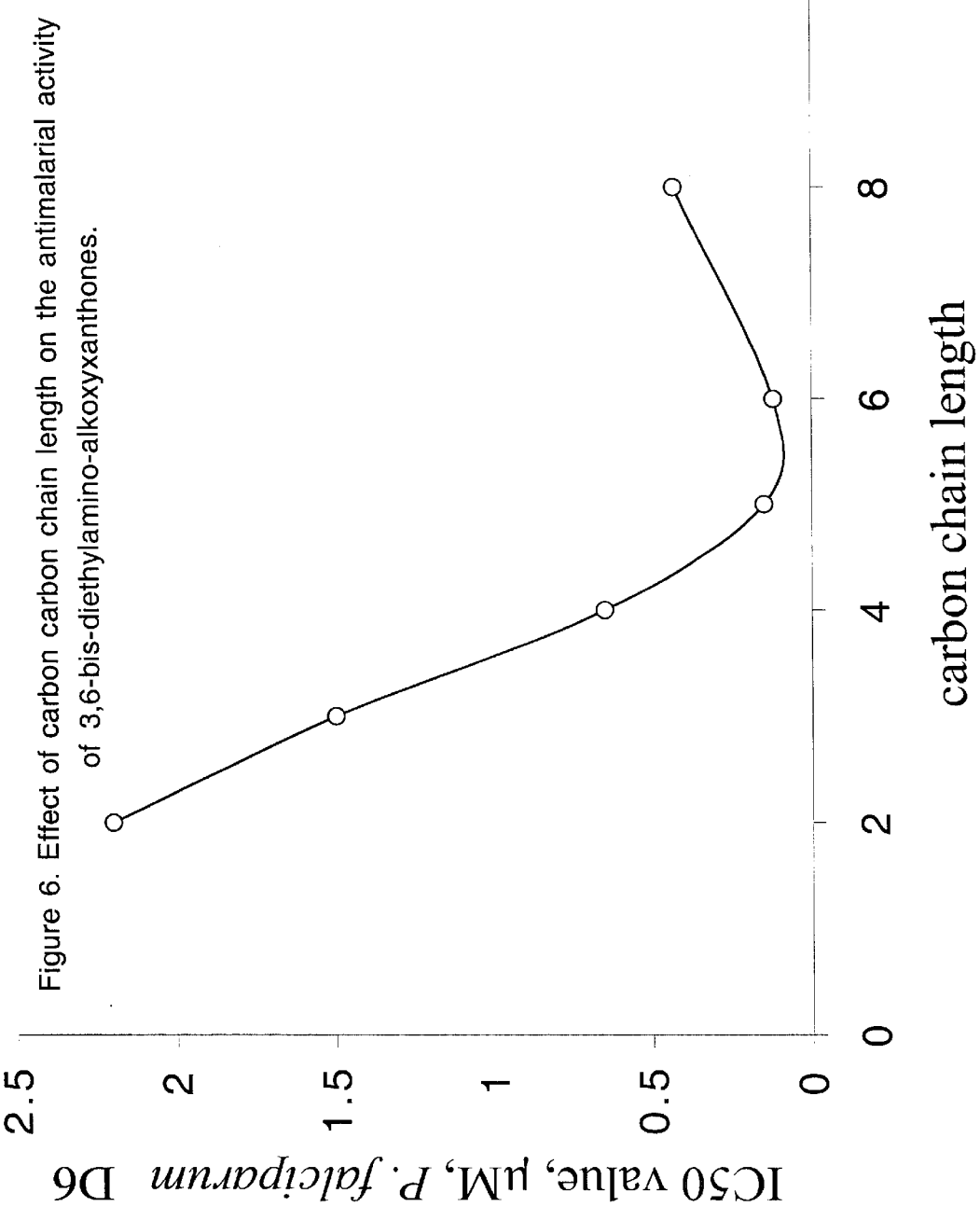
Figure 6. Effect of carbon carbon chain length on the antimalarial activity of 3,6-bis-diethylamino-alkoxyxanthones.

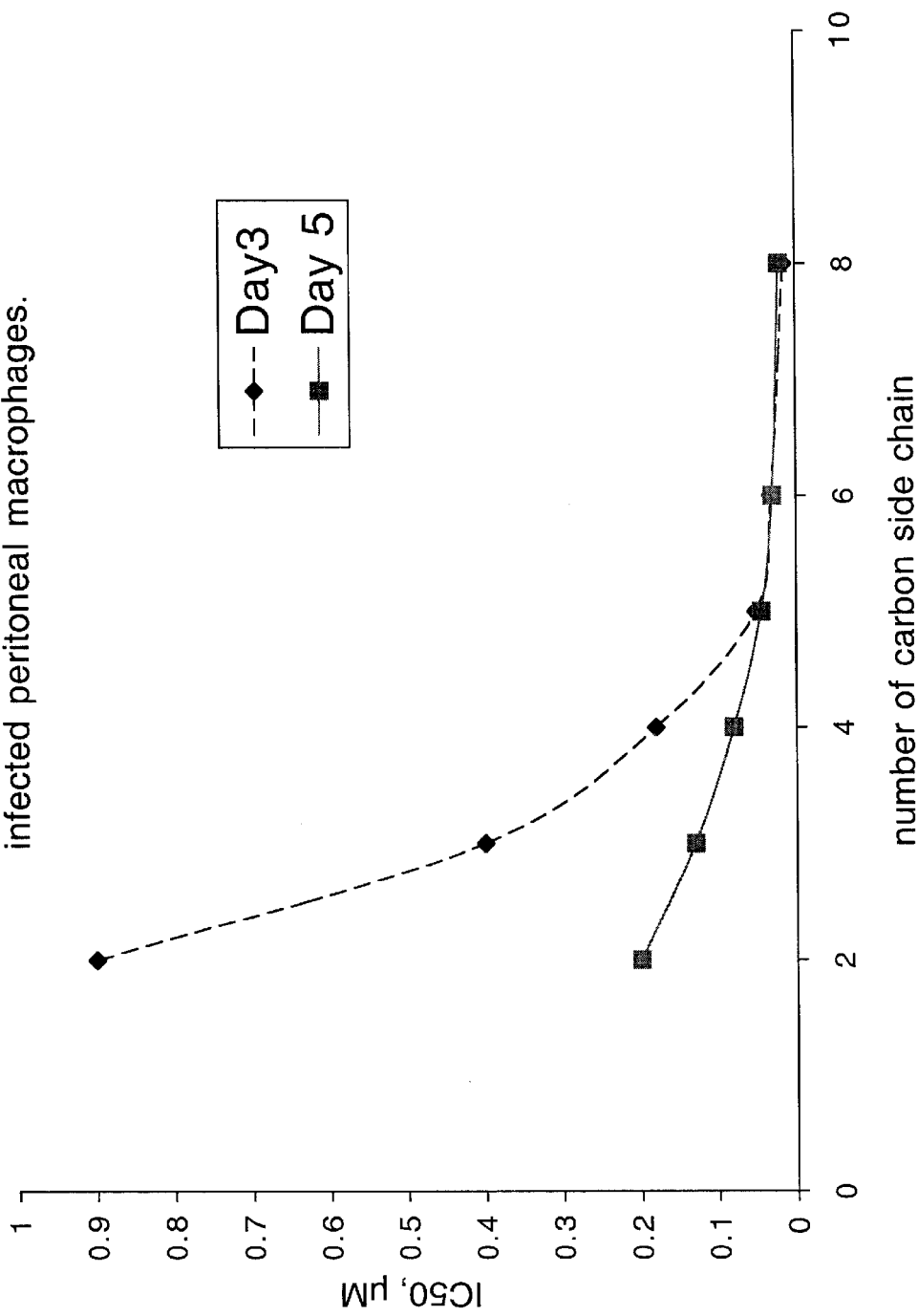
Figure 7. Correlation between carbon chain length and inhibitory activity for the 3,6-bis-diethylaminoalkoxyxanthone series against amastigote-infected peritoneal macrophages.

XANTHONE ANALOGS FOR TREATING INFECTIOUS DISEASES AND COMPLEXATION OF HEME AND PORPHYRINS

This application claims the benefit of Provisional application No. 60/168,784 filed Dec. 2, 1999.

ACKNOWLEDGMENT OF U.S. GOVERNMENT SUPPORT

This invention was made with partial support from the United States Government to Drs. Michael K. Riscoe and David J. Hinrichs through the Veterans Affairs Merit Review System. The U.S. Government may have certain rights to this invention.

BACKGROUND

Protozoan parasites cause diseases such as malaria, trypanosomiasis, Chagas' disease, leishmaniasis, giardiasis, and amoebiasis. These and other parasitic diseases historically have occurred in tropical and sub-tropical areas where they cause widespread suffering of human populations. Although they receive little attention in the Western world, protozoan diseases affect more people worldwide than diseases brought on by any other biological cause (Heyneman, 1988).

Today, malaria remains the most destructive single infectious disease in the developing world. It is responsible for more human death, energy loss, more debilitation, more loss of work capacity, and more economic damage than any other human ailment facing the world today (Heyneman, 1988). The World Health Organization estimates that 1 to 2 million deaths are caused by malaria each year in Africa alone; most of these are children under the age of five (World Health Organization, 1991). In addition, over 300 million people worldwide are believed to be chronically infected, and each year nearly one third of these individuals will suffer acute manifestations of the disease.

Today, the pathologic capacity of protozoa is being increasingly demonstrated in the Western world among AIDS (Acquired Immunodeficiency Syndrome) victims. AIDS depletes the immune system of affected individuals. This allows opportunistic agents to infect AIDS patients, which agents otherwise would be defeated by an active immune system. Several protozoa have proved especially opportunistically infectious in AIDS patients, including *Cryptosporidium parvum, Entamoeba histolytica, Giardia lamblia, Pneumocystis carinii* (which may be a fungal or protozoal pathogen), and *Toxoplasmosis gondii*.

Despite the prevalence and significance of protozoan infections, therapy for these diseases is generally poor or in need of improvement. Many chemotherapeutic agents used to treat protozoan infections are non-specific cytotoxins that are highly toxic and cause severe side effects in patients. However, these drugs are used because there are no better alternatives. For example, giardiasis and amoebiasis are treated using metronidazole (a nitroimidazole), but the mutagenic potential of this drug (Campbell, 1986) and its adverse interaction with alcohol are problematic. For trypanosomiasis and leishmaniasis standard therapies (suramin, melarsoprol, and pentavalent antimonials) are dangerously toxic, occasionally fatal, and often ineffective (Mebrahtu, 1989; Grogl et al., 1992). Other drugs are becoming ineffective due to emerging resistance. In the case of malaria, effective therapy previously has been provided by chloroquine but its efficacy is now threatened by the rapid emergence of drug resistant strains of *Plasmodium falciparum*, the causative agent for the most severe, often fatal, form of the disease (Cowman, 1990). Other protozoal infections such as cryptosporidiosis or Chagas' disease have no proven curative agent.

New therapeutic agents have been developed to treat protozoan infections. For example, Winter et al., U.S. Pat. No. 5,977,077, which is incorporated herein by reference, describes certain xanthone analogs which have sub-10 $\mu$M $IC_{50}$s (some having sub-1$\mu$M $IC_{50}$s), against Plasmodium and Leishmania. Despite these new xanthone analogs useful for treating infectious diseases, particularly protozoan diseases, there still is a need for new agents with comparable or better activities and reduced undesirable attributes, such as toxicity. A diverse array of therapeutic agents also is desireable to prevent or reduce the development of drug-resistant protozoan strains.

SUMMARY

The present invention concerns new compounds which are useful, amongst other things, as antiparasitic agents. Methods for using these new compounds and certain known compounds as anti-parasitic agents are described. These antiparasitic agents form complexes with heme and with porphyrins with superior affinity and are therefore useful in a variety of other applications. The invention also is directed to compounds with broad-spectrum anti-microbial activity.

As a result of studies aimed at developing new antiparasitic agents, the present inventors have discovered that xanthones and a wide range of xanthone derivatives and structurally related compounds, as represented by Formula X below, have potent anti-parasitic activity. The compounds have broad-spectrum anti-microbial activity, including anti-fungal activity against *Candida albicans* and *Aspergillus fumigatus*, and may possess antiviral activity as well.

Formula X

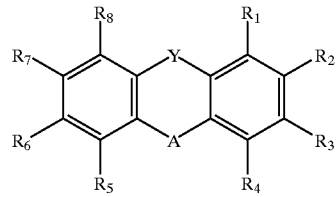

With reference to Formula X, A is oxygen, substituted antimony (stibium), sulfur or N-R' where R' is H, OH, alkyl, haloalkyl, aryl or haloaryl. Examples of substituted antimony groups include antimonial oxides and antimony substituted with hydroxy, chlorine, alkyl and aryl groups (e.g. SbCl, $SbCl_3$, SbOH, Sb(O)(OH)). $R_1$–$R_8$ are independently selected from the group consisting of H, OH, halogen, aryl, arylamine, alkyl, alkene, substituted alkyl (such as alkylamine, alkylthio, haloalkyl, and substituted alkyls having two or more of such substituents), alkoxy, particularly lower alkoxy, such as methoxy, substituted alkoxy (such as alkoxylamine, cycloaminoalkoxy, dialkylaminoalkoxy, such as diethylaminoethoxy, haloalkoxy, and alkoxy groups having two or more of such substituents) amino, ester, ether, nitro groups and O-linked and C-linked carbohydrates. Alkyl and alkoxyl groups often include 10 or fewer carbon atoms in a straight or branched chain, and are referred to as "lower" alkyl or alkoxy groups. Y is selected from the group consisting of NO, NOH, C=O, CH—OH, S=O, and $SO_2$.

Compounds having Y=carbonyl further satisfy Formula X1, where A and $R_1$–$R_8$ are as stated above with reference to Formula X.

Formula X1

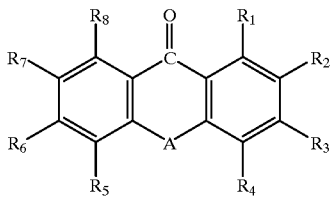

Certain Formula X1 compounds are compounds which also satisfy Formula X2:

Formula X2:

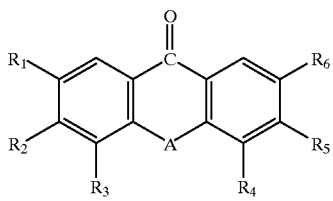

With reference to Formula X2, A is oxygen or sulfur, and $R_1$–$R_6$ are independently selected from the group consisting of H, OH, halogen, aryl, arylamine, alkyl, alkene, substituted alkyl (such as alkylamine, alkylthio, haloalkyl, and substituted alkyls having two or more of such substituents), alkoxy, substituted alkoxy (such as alkoxyamine, alkoxythio, haloalkoxy, and alkoxy groups having two or more of such substituents) amino, ester, ether, nitro groups and O-linked and C-linked carbohydrates. Particular compounds satisfying Formula X2 have $R_1$ and $R_6$ selected from the group consisting of H, —OH, OR, whre R typically is lower alkyl, such as $OCH_3$, and halogen. $R_2$–$R_5$ preferably are selected from the group consisting of side chains linked to the aromatic rings by a carbonyl or thiocarbonyl (i.e., C=O or C=S, respectively), a methylene group (i.e., $CH_2$), oxygen, nitrogen or sulfur, and which further have a positively charged group on the terminal end of the linker. Such side chains are represented by Formula X3.

Formula X3:

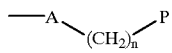

With reference to Formula X3, "A" is carbon, generally a methylene group, a carbonyl, amido, O, S, or N; "n" ranges from 1 to 10, preferably 2 to 8, and even more preferably from about 3 to 7 both branched chains or linear chains; and "P" is a group positively charged at physiological pH, such as amines, amidines, guanidines, cycloalkylamines, such as dicyclopropyl amine, or cycloalkylimines, such as pyrrolidine. "n" is selected to provide a chain length so that "P" preferably can interact with negatively charged groups, such as the propionate groups of heme. Compounds having superior biological activity against Plasmodium and Leishmania have been made using alkoxy amines, such as those represented by Formula X4.

Formula X4:

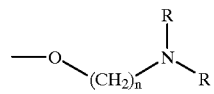

With reference to Formula X4, "n" ranges from about 1 to 10, preferably 2 to 8, and even more preferably from about 3 to 7, including both branched chains and linear chains, and "R" typically is selected from the group of hydrogen and alkyl or cyclo-alkyl groups, preferably lower alkyl groups, such as ethyl groups. Moreover, the R groups of Formula X4 typically, but not necessarily, are the same or linked in a cyclic structure, such as pyrrolidine.

Specific examples of such compounds include 3,6-bis-N,N-diethylaminoxanthone, 3,6-bis-β-(N,N-diethylamino)ethoxyxanthone, 3,6-bis-γ-(N,N-diethylamino)propoxyxanthone, 3,6-bis-δ-(N,N-diethylamino)butoxyxanthone, 3,6-bis-ε-(N,N-diethylamino)amyloxyxanthone, 3,6-bis-ζ-(N,N-diethylamino)hexyloxyxanthone, 3,6-bis-η-(N,N-diethylamino)heptyloxyxanthone, 3,6-bis-θ-(N,N-diethylamino)octyloxyxanthone, 3,6-bis-ι-(N,N-diethylamino)nonyloxyxanthone, and 3,6-bis-κ-(N,N-diethylamino)decyloxyxanthone. 4,5 bis substituted amines and alkoxyamine analogs of these 3,6 bis-substituted compounds also are preferred compounds, including 4,5-bis-N,N-diethylaminoxanthone, 4,5-bis-β-(N,N-diethylamino)ethoxyxanthone, 4,5-bis-γ-(N,N-diethylamino)propoxyxanthone, 4,5-his-δ-(N,N-diethylamino)butoxyxanthone, 4,5-bis-ε-(N,N-diethylamino)amyloxyxanthone, 4,5-bis-ζ-(N,N-diethylamino)hexyloxyxanthone, 4,5-bis-η-(N,N-diethylamino)heptyloxyxanthone, 4,5-bis-θ-(N,N-diethylamino)octyloxyxanthone, 4,5-bis-ι-(N,N-diethylamino)nonyloxyxanthone, and 4,5-bis-κ-(N,N-diethylamino)decyloxyxanthone.

The disclosed invention also is directed to compositions comprising the compounds described above, i.e., compositions including compounds according to Formulae X, X1 and X2. These compositions are useful for the treatment of microbial diseases, such as malaria. These compositions may include materials conventionally used to make therapeutic compositions, and further may include additional therapeutics, particularly those useful for treating parasitic infections, such as malaria and leishmania. Examples, without limitation, of such therapeutics include chloroquine, antifolates, mefloquine, primaquine, cinchona alkaloids, such as quinine, sulfonamides, sulfones, tetracyclines, melarsoprol, nifurtimox, aminoacridines, aminoquinolines, sulfanolimides, pentamidine, stibogluconate, suramin, protease inhibitors, and mixtures thereof.

Also included in the present invention is a method of inhibiting the growth of a microbial pathogen. The method comprises providing a sufficient amount of a compound having Formulae X, X1 and/or X2, or composition comprising such compounds, and contacting the microbial pathogen with such compound(s) or composition(s). The present method is useful for inhibiting microbial growth in vivo and in vitro. In one aspect, the present invention provides a method for treating a patient having a microbial infection. "Patient" includes, without limitation, humans and animals, particularly economically important animals, such as livestock and avians, particularly poultry infected with protozoans, such as Eimeria. The method comprises administering to the patient a therapeutically effective amount of a compound or compounds, or composition comprising such compound or compounds, satisfying Formulae X, X1 and/or X2.

Another aspect of the present invention is the discovery that certain compounds having the xanthone ring structure depicted in Formulae X, X1 and/or X2 bind to, and inhibit the aggregation of, heme. A number of pathogens, including Plasmodium, a causative agent of malaria, degrade hemoglobin to obtain amino acids, and in so doing liberate toxic heme (Olliaro and Goldberg, 1995). To avoid the toxic effects of the liberated heme, these pathogens have evolved a mechanism for "aggregation" of heme units to form hemozoin. (Pagola, Stephens, P. W., Bohle, D. S., Kosar, A. D., Madsen, S. K., Nature, "The Structure of Malaria Pigment Beta Haematin," 404:307–310 (2000). The compounds disclosed herein which are shown to inhibit heme aggregation may thus be used to block heme aggregation and therefore to treat infections caused by these pathogens. These heme complexing compounds may kill pathogens by preventing these organisms from gaining access to the host's supply of heme iron, or by causing a build-up of toxic levels of heme in the organism. The compounds also may bind to heme of other metalloporphyrins and block one-electron transfer reactions.

Compounds which are disclosed herein to inhibit heme aggregation may be represented by the structure

where X is a group capable of interacting with the iron atom in heme (e.g., carbonyl, N→O, N—OH, $SO_2$, and S=O); Y is a substantially planar aromatic system capable of interacting with the porphyrin ring of heme, possibly through overlapping pi—pi orbitals; and Z represents one or more groups capable of interacting with at least one carboxylate side group of heme. In preferred embodiments, these compounds are Formula X2 compounds.

The present invention also is directed to compositions useful for treating diseases, such as malaria, which are caused by pathogens that polymerize heme. The compositions include a compound according to Formula X2. Also included in the present invention is a method for inhibiting the growth of such a pathogen comprising providing a sufficient amount of a Formula X2 compound and contacting the pathogen with this compound. Such a method is applicable to inhibit pathogen growth in vivo and in vitro. In one aspect, the present invention provides a method for treating a patient having malaria, the method comprising administering to the patient a therapeutically effective amount of a compound according to Formula X2.

The invention also contemplates that Formula X, X1 and X2 compounds can be administered to patients in a pro-drug form. One example of a class of such prodrugs is correspondingly substituted benzophenones. These substituted benzophenones may react under physiological conditions to produce active compounds (i.e., the corresponding xanthone derivatives) satisfying Formulae X, X1 and/or X2 (Winter et al., 1996).

Related to the ability of Formula X, X1 and X2 compounds to bind to heme is the ability of these compounds to bind to a porphyrin. This porphyrin binding activity may be exploited in the development of treatments for porphyria. In addition, the binding between the Formula X, X1 and/or X2 compounds and heme/porphyrins may find applications in other contexts, such as laundry detergents (e.g., to enhance the ability of detergents to remove blood or grass stains) or in agricultural products that bind chlorophyll (a metalloporphyrin) and perturb plant growth.

BRIEF DESCRIPTION OF THE FIGURES

FIG. 6 is a graph of chain length versus $IC_{50}$ for P. falciparum.

FIG. 7 is a graph of number of carbons in compound side chains for 3,6-bis-diethylaminoalkoxyxanthones versus $IC_{50}$ values against amastigote-infected peritoneal macrophages.

DETAILED DESCRIPTION

I. Definitions

Figure 1:
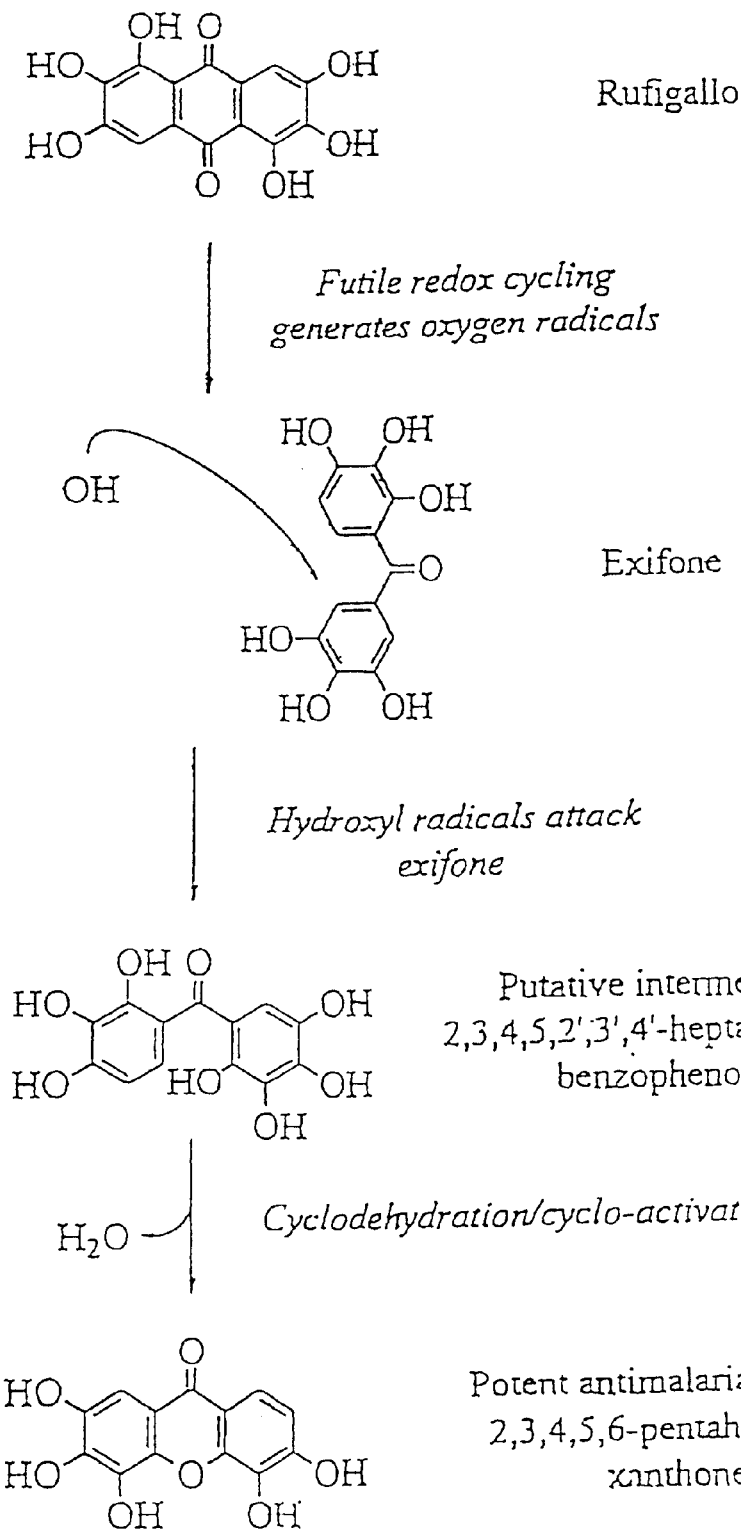
FIG. 1 illustrates a proposed mechanism for the formation of 2,3,4,5,6-pentahydroxyxanthone from the metabolic activation of exifone by rufigallol within a red blood cell infected with the Plasmodium parasite.

The phrases "a compound according to Formula X" and "a xanthone derivative according to Formula X" refer to a compound having the following structure:

Formula X:

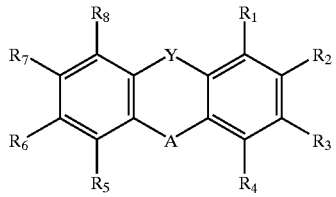

With reference to Formula X, A is oxygen, substituted antimony (stibium), sulfur or N-R' where R' is H, OH, alkyl, haloalkyl, aryl or haloaryl. Examples of substituted antimony groups include antimonial oxides and antimony substituted with hydroxy, chlorine, alkyl and aryl groups (e.g. SbCl, $SbCl_3$, SbOH, Sb(O)(OH)). $R_1$–$R_8$ are independently selected from the group consisting of H, OH, halogen, aryl, arylamine, alkyl, alkene, substituted alkyl (such as alkylamine, alkylthio, haloalkyl, and substituted alkyls having two or more of such substituents), alkoxy, particularly lower alkoxy, such as methoxy, substituted alkoxy (such as alkoxylamine, cyclio aminoalkoxy, dialkylaminoalkoxy, such as diethylaminoethoxy, haloalkoxy, and alkoxy groups having two or more of such substituents) amino, ester, ether, nitro groups and O-linked and C-linked carbohydrates. Alkyl and alkoxyl groups often include 10 or fewer carbon atoms in a straight or branched chain, and are referred to as "lower" alkyl or alkoxy groups. Y is selected from the group consisting of NO, NOH, C=O, CH-OH, S=O, and $SO_2$.

References to compounds such as "an X compound" refer to the compounds shown in the Summary of the Invention section above. Where a particular substituent in the formula is intended, it is given parenthetically. For example X (A=O) refers to a compound according to Formula X where the A substituent is oxygen.

Compounds of the present invention which may be used to inhibit heme polymerization (and therefore to treat certain parasitic diseases such as malaria) are referred to as "Formula X compounds". A Formula X compound is a compound broadly defined as:

where X is a group capable of interacting with the iron atom in heme; Y is a substantially planar aromatic system capable of interacting with the porphyrin ring of heme through overlapping pi—pi orbitals; and Z represents one or more groups capable of interacting with at least one carboxylate side group of heme, such as amine functionalities that are protonated at physiological pH.

In preferred embodiments, Formula XH compounds also have the following X1 structure, where Y=carbonyl (i.e., C=O), and A and $R_1$–$R_8$ are as stated above with reference to Formula X.

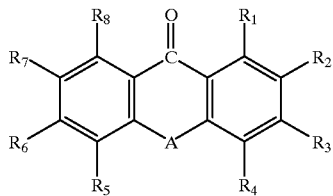

More specifically, $R_1$–$R_2$ and $R_7$–$R_8$ are independently selected from the group consisting of H, OH, and halogen, most typcially hydrogen. At least one member (but preferably both) of the $R_3/R_6$ or R4/R5 substituent pairs (and preferably both) is selected from the group consisting of amino, substituted amino, alkylamino, substituted alkyl amino, arylamino, amidinium, alkylamidinium, guanidinium, alkylguanidinium, hydroxy, alkylhydroxy, alkoxyhydroxy, alkoxyamine, alkoxy-substituted amine, azido, carboxylic esters of hydroxy, alkylhydroxy and alkoxyhydroxy groups, COOH, alkyl-COOH, $CONH_2$ and alkyl-CONH2. The other member of the $R_3/R_6$ or R4/R5 substituent pairs is selected from the group consisting of H, OH, halogen, aryl, arylamine, alkyl, substituted alkyl (such as alkoxy, alkylamine, alkylthio and haloakyl), amino, substituted amino, ester and nitro groups, O-linked and C-linked carbohydrates, alkylamino, substituted alkyl amino, arylamino, amidinium, alkylamidinium, guanidinium, alkylguanidinium, alkylhydroxy, alkoxyhydroxy, alkoxyamine, alkoxy-substituted amine, azido, carboxylic esters of hydroxy, alkylhydroxy and alkoxyhydroxy groups, COOH, alkyl-COOH, $CONH_2$ and alkyl-$CONH_2$.

As used herein, the term "alkyl" encompasses alkanes, alkenes and alkynes, including linear and branched forms, isomers and stereoisomers. In certain embodiments, an alkyl is a lower alkyl, meaning an alkyl having 10 or fewer carbon atoms.

The terms "ester" and "esterification" are used herein as ordinarily understood in the chemical arts, see, for example, Morrison and Boyd, *Organic Chemistry*, Allyn & Bacon, Inc., Boston, 1983, herein incorporated by reference. Thus, an ester may be formed by, for example, the combination of an alcohol and an organic acid, with the concurrent elimination of water. The process of forming an ester is termed "esterification." For example, the formula X1 compound 2,3,4,5,6-pentahydroxyxanthone may be esterified by reaction with appropriate acid anhydrides resulting in the net replacement of one or more hydroxyl substituents with ester substituents including, but not limited to: acetoxy ($OCOCH_3$); propionyloxy ($OCOCH_2CH_3$); and butyryloxy $OCO(CH_2)_2CH_3$) substituents. Esters produced in this manner may be generally represented by the formula $OCO(CH_2)_nCH_3$ wherein n is zero or a positive integer. In particular embodiments, the term "ester" as used herein refers to an ester wherein n is 1–10.

A "microbial pathogen" is a microorganism capable of causing disease in an animal. The term "microbial pathogen" includes bacterial, mycoplasmal, fungal, viral, helminth and protozoan organisms. "Parasites" are a subclass of microbial pathogens, being protozoan and helminth organisms that are capable of invading, colonizing and, under appropriate conditions, causing disease in an animal. Examples of parasites include, without limitation, *Leishmania donovani*, *Leishmania mexicana*, *Plasmodium falciparum*, *Giardia lamblia*, *Schistosoma mansonic*, *Trypanosoma gambiense* and *Trypanasoma cruzi*. See generally, Robbins et al, Pathologic Basis of Disease (Saunders, 1984) 273–75, 360–83.

A "microbial infection" is a disease caused by a microbial pathogen.

A compound having "anti-microbial activity" is a compound that is capable of inhibiting the growth of a microbial pathogen as determined in in vivo or in vitro assays of the kind normally employed to determine minimum inhibitory concentrations (MICs) or 50% inhibitory concentrations ($IC_{50}$) of an antimicrobial agent.

An "oxidant agent" is an agent having the ability to produce or liberate free radical oxygen species or to render parasites or their host cells more susceptible to oxygen radical attack, or having the capacity of oxidizing another compound. Examples of oxidant agents in this general sense include ascorbic acid, hydrogen peroxide, primaquine (or its metabolites) and gamma radiation.

II. Biological Methods

A. Methods for Determining Biological Activity

The anti-parasitic activity of the compounds of the present invention was determined using three different parasites: *Plasmodium falciparum*, a causative agent of malaria; and *Leishmania donovani* and *Leishmania mexicana*, causative agents of leishmaniasis. The activity of the compounds against yeast was determined using *Candida albicans*.

1. Assay for Anti-Malarial Activity

The D6 strain of *P. falciparum* was cultured in Group $A^+$ human erythrocytes and suspended at a 3.3% hematocrit in RPMI-1640 (Gibco, Grand Island, N.Y.) (containing 4 g/L glucose, 50 mg/L gentamicin and 10% group $A^+$human serum), buffered with 25 mM HEPES and 25 mM $NaHCO_3$ (Trager and Jensen, 1976). Cultures were maintained at 37° C. in a gas mixture of 5% oxygen, 5% $CO_2$, and 90% nitrogen.

The in vitro anti-malarial activities of 2,3,4,5,6-pentahydroxy-xanthone and other Formula X1 were measured by the [$^3$H]-ethanolamine incorporation method as described in Elabbadi et al., 1992, with minor modifications. [$^3$H]-ethanolamine was obtained from American Radiolabeled Chemicals, Inc., St. Louis, Mo. Experiments were conducted in 96 well plates in a total volume of 200 μl at a final red blood cell concentration of 2% (v/v). An initial parasitemia of 0.2 to 0.5% was attained by addition of normal uninfected red cells. Radiolabeled ethanolamine was added after 48 hours of incubation and the experiment was terminated after 72 hours by collecting the cells onto glass fiber filters with an automated multiwell harvester.

Stock solutions of the various Formula X1 compounds were dissolved in DMSO at a concentration of 1 mM and diluted in complete medium (including 10% human serum) to provide 10X stock concentrations in the range of 1 to 10,000 nM. The concentration of the formula X1 compound giving 50% inhibition of label incorporation ($IC_{50}$) relative to control (i.e., drug-free) conditions was calculated from the dose-response curve.

2. Assay for Anti-Leishmania Activity a. Promastigote Stage

*Leishmania donovani* was cultivated in Schneider's medium (Gibco, Grand Island, N.Y.) according to the methods described by Grogl et al. (1992). The in vitro susceptibility of *L. donovani* to Formula X1 compounds was determined using the radiolabeled thymidine uptake assay essentially as described by Grogl et al. (1992). Briefly, promastigotes were cultivated at 25° C. in Schneider's medium supplemented with 20% inactivated fetal calf serum and 100 $\mu$g/mL of gentamicin. Cells were maintained in log phase by seeding at $1 \times 10^6$/mL with subculturing when cultured densities approached $4 \times 10^7$/mL before reaching their maximal density. For the assay, early log phase promastigotes were counted on a hemacytometer and resuspended at a concentration of $1-2 \times 10^6$ cell/mL in assay media (Schneider's medium plus 10% fetal bovine serum). Ten-fold serial dilutions of each test compound were prepared as described above and added to 180 $\mu$L of the parasite suspension. After incubation for 24 hours at 25° C., methyl-$^3$H-thymidine was added to each sample for a final concentration of 1–2 $\mu$Ci per well. Each sample was then incubated for an additional 18 hours prior to harvesting. After this incubation time, each sample was aspirated onto a filter mat, washed thoroughly with deionized water, dried and then counted in a scintillation counter with scintillation cocktail.

b. Intracellular Amastigote Stage

Bone-marrow-derived macrophages (BALB/c) were cultured with L-cell-conditioned medium for 5–7 days at 35° C. After this period of incubation, mature macrophages were transferred to Labtek 4-chamber slides containing DMEM (Dulbecco's Modified Eagle's Medium) and 10% fetal calf serum. 50,000 cells were seeded in each chamber and allowed to attach overnight at 37° C. in a humidified incubator flushed with 5% $CO_2$. On the next day the macrophages were infected at an MOI (Multiplicity of Infection) of 10:1 with stationary promastigotes of *L. mexicana*. After twenty-four hours, the medium was removed and fresh medium was added containing various drug concentrations (0–5 $\mu$M). Following incubation for an additional forty-eight hours, one set of slides were fixed in methanol, dried, and stained with Giemsa stain. Fresh medium and drug were added to a parallel set of chamber slides and incubated for another 48 hours before staining. Therefore, $IC_{50}$ values were obtained for each drug at 48 hours and 96 hours of drug exposure. Microscopic inspection permitted determination of % of infected macrophages and the number of amastigotes per 100 macrophages. The $IC_{50}$ value is that concentration of drug that reduces the amastigote number by 50% relative to drug-free controls. Results also were obtained in parallel fashion with macrophages.

3. Assay for Anti-Candida Activity

The minimum inhibitory concentration (MIC) of formula X1 compounds against a clinical isolate of *Candida albicans* was determined using the following method. As used herein MIC represents the concentration of formula X1 compound that completely inhibits growth of *Candida albicans* over the course of a 15–18 hour incubation period. The determination of this concentration is made by visual inspection; there is no visible growth in a tube containing the MIC of the formula X1 compound whereas visible growth is present in tubes containing sub-MIC concentrations of the compound.

*Candida albicans* was grown to midlog-phase in Luria-Bertani broth (10 grams Bacto-tryptone, 5 grams Bacto-yeast extract and 10 grams NaCl per liter) and then inoculated into sterile test tubes containing LB broth to an initial density of $10^3$/ml. The formula X1 compound to be tested is dissolved in dimethylsulfoxide (DMSO) at a concentration of 1 mM and added to each tube at serial dilutions (1 $\mu$M, 10 $\mu$M, 25 $\mu$M, 50 $\mu$M, 100 $\mu$M and 0 $\mu$M). The tubes are incubated at 35° C. for 15–18 hours and then visually inspected.

B. Affinity of Drugs for Heme

1. In Vitro Heme Aggregation Assay

Heme polymerization was carried out in 0.02 M phosphate buffer, pH 5.2 at 37° C. in the absence of protenis. A 10 mM stock solution of hemin chloride in 0.1 M NaOH wa prepared freshly and incuated at 37° C. for at least 1 hour to effect complete dissolution. Xanthones were dissolved in dimethylformamide at 10 mM and diluted into 10 ml of pre-warmed phosphate solution to a final concentraion of 25 $\mu$m. Polymerization wa sinitated gy addition of 25 $\mu$l of the hemin stock solution to the test sample to yuiled a final concentratin of 25 $\mu$M heme. 25 $\mu$l of dimethylformaide wa added to the control smample. After 7, 30, 60, 120 and 190 minutes of incugation at 37° C., a 1 ml aliquot was withdraqwn, tranferred into an Eppendorf tube, and centrifugted at 14,000 g for 2 minutes at room temperature to pellet the precipitate. The soluble fraction was then transferred to a semi-microcuvette (polymethyacrylate, VER), and its absoprtion was measured at 360 nm against a blank of the test compound in buffer. Control experiments indiated that (1) the pH of the phosphate solution did not change upon addition of the reagents or during thepolymerization process, and (ii) the amount of dimethylformamide used in this assay did not significantly affect the rate of polymerization. To estimate the effect of test compounds on heme polymerization at a given time of incubation, the percentage of soluble hemin remaining in the sample was calculated using the following formula: % sol. hemin=$[A_{(drug+hemin)t} - A_{(drug)t}]/[A_{(hemin)t=0}] \times 100\%$ where $A_{(drug+hemin)t}$ is the absorption (360 nm) of the soluble fraction in the drug-hemin sample after various times of incubation; $A_{(drug)t}$ is the absorption of the drug alone; and $A_{(hemin)t=0}$ is the absorption of the hemin control sample (25 $\mu$M) measured immediately upon addition of the hemin stock solution.

The dose-dependent inhibition of heme polymerization was evaluated as described above except the concentration of each drug was varied in the range of 0 to 1 mM. The reactions were allowed to proceed for 2 hours in a 37° C. waterbath. After incubation, the polymer was pelleted as described above and the absorption (360 nm) of each soluble fraction was measured against a blank containing the drug alone in buffer. The $IC_{50}$ values were determined by non-linear regression analysis of the dose-response curves of percent inhibition of heme polymerization vs. drug concentration.

III. Production of 2,3,4,5,6-pentahydroxyxanthone in Parasitized Erythrocytes Treated with Rufigallol and Exifone As disclosed in Winter et al. (1996), rufigallol (1,2,3,5,6, 7,-hexahydroxy-9,10-anthraquinone) is a potent antiparasitic agent and, when rufigallol is combined with exifone (2,3,3',4,4',5'-hexahydroxybenzophenone), a synergistic effect is observed. The synergy between rufigallol and exifone is noted to produce about a 350-fold increase in potency against malaria Plasmodium parasites.

One aspect of the present invention is the discovery that rufigallol and exifone interact in the parasitized erythrocyte to yield 2,3,4,5,6-pentahydroxyxanthone, and that this compound is a potent anti-malarial agent. FIG. 1 shows a possible mechanism by which 2,3,4,5,6-pentahydroxyxanthone could be produced when rufigallol and exifone are present in a parasitized erythrocyte. Basically, rufigallol is proposed to enter the parasitized erythrocyte, leading to the formation of hydrogen peroxide in a manner similar to the well-documented redox cycling behavior of hydroxynaphthoquinones. In the presence of catalytic quantities of adventitious iron or iron chelates, such as heme, (liberated as a result of the Plasmodium parasite digesting hemoglobin, Atamna and Ginsburg, 1993), hydrogen peroxide is readily decomposed to hydroxyl radicals (Goldstein et al., 1993; Aust et al., 1985). These highly reactive radicals are proposed to attack exifone and transform the diphenyl compound into 2,3,4,5,6-pentahydroxyxanthone.

As reported in U.S. application Ser. No. 08/520,694, the anti-malarial activity of exifone can be potentiated by a very wide range of oxidant agents, including ascorbic acid, artemisinin and doxorubicin. This observation is consistent with the mechanism proposed above. The production of 2,3,4,5,6-pentahydroxyxanthone in the proposed reaction scheme was confirmed by incubating exifone with ascorbic acid in the presence of iron salt and oxygen in a buffered solution at 37–40° C. (the "Udenfriend system," Brodie et al., 1954; Maisant et al., 1983; Udenfriend et al., 1954). Samples were removed from the reaction at various time points, lyophilized and extracted with acetone. The solubilized products were then methylated by addition of excess potassium carbonate and dimethylsulfate in acetone and analyzed by gas chromatography-mass spectrometry. A peak corresponding to the methoxy derivative of 2,3,4,5,6-pentahydroxyxanthone was detected.

IV. Synthesis and Anti-Microbial Activity of 2,3,4,5,6-pentahydroxyxanthone 2,3,4,5,6-pentahydroxyxanthone was produced using the following method.

A mixture of 1,2,3-Trimethoxybenzene (1.48 g) and 2-hydroxy-3,4,5-trimethoxybenzoic acid (2.00 g) is stirred in 40 ml of ≈9% solution of $P_2O_5$ in methanesulfonic acid at room temperature in a stoppered flask for 4 hours. The 2-hydroxy-3,4,5-trimethoxybenzoic acid was obtained by the method of Mayer and Fikentscher (Mayer and Fikentscher (1956) Chem. Ber. 89:511) from 3,4,5-trimethoxybenzoic acid by bromination and then copper-catalyzed replacement of bromine (by OH) of 2-bromo-3,4,5-trimethoxybenzoic acid. The resultant orange mixture is poured onto crushed ice (500 ml) producing an unfilterable gummy precipitate. This crude product is then subjected to base-catalyzed ring closure by heating in a beaker in 100 ml of 40% ethanol and 10 ml of 10N NaOH just below boiling point. As the mixture reaches 80° C., a white flocculent product appears. The temperature is maintained just below the boiling point and the volume is kept constant by addition of water. After 5 hours, the supernatant is bright yellow and a mass of the precipitate has formed. Heating is continued for 4 more hours. Cooling, filtering (by suction) and washing with water afforded 1.37 g of analytically pure 2,3,4,5,6-pentainethoxyxanthone (yield approximately 45% relative to benzoic acid). This base-catalyzed ring closure is illustrated below:

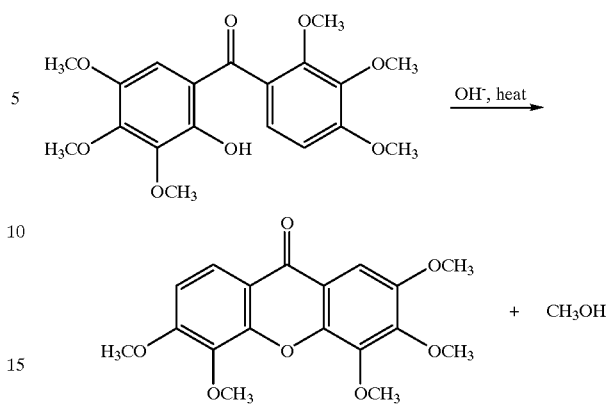

2,3,4,5,6-pentahydroxyxanthone is then obtained by boron tribromide treatment (200 ml of a 0.8 M solution in $CH_2Cl_2$) as the pentamethyl ether (0.45 g) is stirred at room temperature for 24 hours. After this period, the solution is poured into 100 ml of water and stirred for approximately 45 minutes before the precipitate is collected by centrifugation. The supernatant is then decanted, the precipitate is shaken with water and centrifuged again. The final product is obtained by freeze-drying of the wet precipitate to produce an orange powder (0.290 g, 81%).

The anti-malarial activity of 2,3,4,5,6-pentahydroxyxanthone was determined by the method described above. The $IC_{50}$ was determined to be 0.4–0.5 $\mu$M. Chloroquine, a standard anti-malarial agent has an $IC_{50}$ in this assay system of approximately 0.04 $\mu$M.

The anti-leishmanial activity of 2,3,4,5,6-pentahydroxyxanthone was determined by the intracellular amastigote method described above. The $IC_{50}$ was determined to be approximately 5 $\mu$M or 0.001 mg/ml. Mangostin, a naturally occurring xanthone, exhibited an $IC_{50}$ of 1 $\mu$M (or 0.00041 mg/ml) in this same system. Grögl et al. (1992) report that two commonly used anti-leishmanial drugs, Pentostam and Glucantine, have $IC_{50}$ values in the range of approximately 0.1–2 mg/ml.

The MIC of 2,3,4,5,6-pentahydroxyxanthone against *Candida albicans*, determined using the method described above was found to be approximately 37.5 $\mu$M. This corresponds to an $IC_{50}$ of approximately 10 $\mu$g/ml.

V. Synthesis and Anti-Microbial Activity of 2,3,4,5,6-pentaacetoxyxanthone

Although 2,3,4,5,6-pentahydroxyxanthone was found to have potent anti-malarial activity, the highly acidic nature of the 3 and 6 hydroxy groups of this compound (i.e. the $R_3$ and $R_6$ positions) could lead these groups to be highly ionized at physiological pH values. Such ionization likely would reduce the rate at which the compound could cross biological membranes, thereby lowering the uptake of the compound into parasitized erythrocytes. Accordingly, two derivatives of 2,3,4,5,6-pentahydroxyxanthone were produced which were expected to be more stable and uncharged above neutral pH: a pentacetoxy (i.e. esterified) derivative, 2,3,4,5,6-pentaacetoxyxanthone, as well as a methoxy (i.e. methyl ether) derivative, 2,3,4,5,6-pentamethoxyxanthone. The activity of these two derivatives against *P. falciparum* was measured.

As shown in Table 1, the addition of the ether (methoxy) groups essentially eliminated the anti-malarial activity of the compound, resulting in an $IC_{50}$ of >100 $\mu$M. This reduction in activity is believed to be attributable to the extreme stability of the methoxy groups; the methoxy group is less amenable to enzymatic cleavage under physiological conditions.

The pentaacetoxy derivative was produced by heating 2,3,4,5,6,-pentahydroxyxanthone in acetic anhydride in the presence of a catalytic amount of sulfuric acid, followed by recrystallization. In contrast to the methoxy derivative, the esterified 2,3,4,5,6,-pentaacetoxyxanthone was several times more potent than 2,3,4,5,6-pentahydroxyxanthone (exhibiting an IC$_{50}$ of approximately 0.075 $\mu$M). The enhanced activity of the esterified compound is postulated to be due to the ability of the compound to cross membranes (due to its neutral charge at physiological pH). Esters are also known to be amenable to enzymatic cleavage under physiological conditions. Accordingly, it is expected that the pentaacetoxyxanthone enters the cell where it is enzymatically cleaved to produce pentahydroxyxanthone.

VI. Synthesis and Anti-Microbial Activity of 2,3,4,5,6,7,-hexahydroxyxanthone

The newly discovered anti-malarial activity of 2,3,4,5,6-pentahydroxyxanthone prompted the investigation of other xanthones and related compounds. One such related compound was 2,3,4,5,6,7,-hexahydroxyxanthone which was prepared using the following method.

2-hydroxy-3,4,5-trimethoxybenzoic acid (1.14 g, 0.005 mol) and 1,2,3,4-tetramethoxybenzene (0.99 g, 0.005 mol) and 25 ml of a 9% solution of P$_2$O$_5$ in methanesulfonic acid were shaken in a 50 ml cylindrical glass tube with a Teflon-lined screw-cap at room temperature for 54 hours. The dark orange mixture was then poured onto crushed ice (150 ml). After melting, the product was extracted with methylene chloride (3×40 ml). After removal of the solvent, the residue was chromatographed on silica gel (30 g) with CH$_2$Cl$_2$. Of the three fractions obtained (the eluent was monitored by thin-layer chromatography), the middle one was uniform and left pure 2-hydroxy-3,4,5,2',3',4',5'-heptamethoxybenzophenone (0.51 g, 25%) as a yellow oil upon evaporation of the solvent. This was dissolved in 100 ml 75% alcohol whereafter 5 ml of 10N NaOH were added and the mixture was heated to boiling in a beaker for three hours; the volume was kept at 100 ml by occasional addition of water. The mixture was then transferred to a 250 ml round bottom flask and refluxed for another 17 hours. After cooling, suction filtration yielded 0.36 g of 2,3,4,5,6,7-hexamethoxyxanthone as a white product (small needles, matted, 77%). In a deprotection procedure, similar to the one described above for pentamethoxyxanthone, 0.42 g of the hexamethoxyxanthone produced 0.296 g of hexahydroxyxanthone (91%) as a pale yellow powder. It was found advantageous to circumvent the need for centrifugation by stirring the methylene chloride-water mixture (from the quenching of the BBr$_3$-solution) in a wide-mouthed container for several hours, leading to the evaporation of the methylene chloride; the mixture is then easily filterable.

The antimalarial activity of 2,3,4,5,6,7-hexahydroxyxanthone was determined by the method described above. The IC$_{50}$ was determined to be 0.075 $\mu$M. The IC$_{50}$ of this compound against Leishmania was determined to be approximately 5 $\mu$M. The MIC of the compound against Candida albicans was determined to be approximately 37.5 $\mu$M, corresponding to an IC$_{50}$ of approximately 10 $\mu$g/ml.

VII. Scope of Formula X Compounds

The inventors have discovered that a wide range of compounds related to 2,3,4,5,6-pentahydroxyxanthone have anti-microbial activity. These compounds can be represented by Formula X

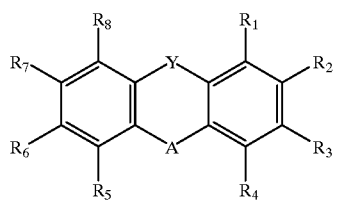

With reference to Formula X, A is oxygen, substituted antimony (stibium), sulfur or N-R' where R' is H, OH, alkyl, haloalkyl, aryl or haloaryl. Examples of substituted antimony groups include antimonial oxides and antimony substituted with hydroxy, chlorine, alkyl and aryl groups (e.g. SbCl, SbCl$_3$, SbOH, Sb(O)(OH)). R$_1$–R$_8$ are independently selected from the group consisting of H, OH, halogen, aryl, arylamine, alkyl, alkene, substituted alkyl (such as alkylamine, alkylthio, haloalkyl, and substituted alkyls having two or more of such substituents), alkoxy, particularly lower alkoxy, such as methoxy, substituted alkoxy (such as alkoxylamine, cycloaminoalkoxy, dialkylaminoalkoxy, such as diethylaminoethoxy, haloalkoxy, and alkoxy groups having two or more of such substituents) amino, ester, ether, nitro groups and O-linked and C-linked carbohydrates. Alkyl and alkoxyl groups often include 10 or fewer carbon atoms in a straight or branched chain, and are referred to as "lower" alkyl or alkoxy groups. Y is selected from the group consisting of NO, NOH, C=O, CH-OH, S=O, and SO$_2$.

The activities of various Formula X compounds against the Plasmodium falciparum parasite are shown in Table 1 (reproduced below) of U.S. Pat. No. 5,977,077, which is incorporated herein by reference. The activities of various Formula X compounds against Leishmania donovani are shown in Table 2 of U.S. Pat. No. 5,977,077. For comparison, Table 2 also shows the activity of stibogluconate, a standard anti-leishmanial. The activities of various Formula X compounds against Plasmodium falciparum and intracellular are provided in Table 3. The activities of various Formula X compounds against Plasmodium falciparum and intracellular Leishmania mexicana parasites correlated to their affinity for heme (hematin) are provided in Table 3.

A. Rational Design Improvements and Enhanced Activity of Formula x Compounds

Based on a molecular model that was constructed depicting the carbonyl-iron coordination, the π-π stacking of coplanar aromatic molecules, and hydrogen bonding between the hydroxyl substituents of 4,5-dihydroxyxanthone and hematin's propionate groups, we proceeded with synthesis of nitrogenated xanthones. 3–6-bis-diethylaminoxanthone (referred to as "C0" in Table 4) was prepare but it exhibited only weak antimalarial activity (IC$_{50}$≈20 $\mu$M) against P. falciparum. These findings indicated that the protonatable species could not be directly attached to the aromatic ring or in conjugation with the carbonyl moiety. Presumably this arrangement results in formation of bis-cations (formed once the drug enters the acidic environment of the parasite digestive vacuole) which draw electrons away from the carbonyl and diminish the interaction with heme iron.

A decision was made to retain the oxygen atom (a conjugatively electron-donating species) as a bridge for an R-group containing the protonatable nitrogen. Molecular models constructed from a ball and stick kit reproducing bond lengths, geometries, and angle strains demonstrated that an optimal chain length in the range of C4 to C6 would permit a relatively strain-free, close association between the ammonium ions of the xanthone and the carboxylate groups of heme. For comparative purposes, the straight-chain di-substituted series from $C_2$ to $C_8$ (i.e., excepting $C_7$), each with a terminal diethylamino group was prepared. Shown in Table 4 is the remarkable relationship between chain length and antimalarial activity within the series . . . and the extraordinary potency of the C5 (3,6-bis-ω-diethylaminoamyloxyxanthone) and C6 (3,6-bis-ω-diethylaminohexyloxyxanthone) congeners. FIG. 6 displays the correlation graphically with minimum $IC_{50}$ values of ≈0.1 μM recorded for the pair against the mefloquine resistant D6 clone of *P. falciparum*. The degree of potency was found to be the same against the multidrug resistant W2 strain.

B. Antileishmanial Activity of Modified Xanthones Against Leishmania Parasites in the Amastigote Stage of Development Intracellular amastigote studies. Leishmania parasites exhibit a dimorphic life cycle, existing as promastigotes in the insect vector and as amastigotes in the phagolysosome of the host macrophage. Because the amastigote stage is the only relevant clinical form of the parasites, we examined the activity of the nitrogenated xanthones against the heme-auxotrophic, intracellular amastigote form of *L. mexicana*. Stationary promastigotes of *L. mexicana* M379 rapidly invaded murine peritoneal macrophages obtained from BALB/c mice and incubated at 35° C. producing heavily burdened cells with 10 to 50 amastigotes per macrophage within 24 hours. An experiment was performed to investigate the ability of selected xanthones to reduce the number of intracellular amastigotes using this model. The $IC_{50}$ value is that concentration of drug required to reduce the intracellular parasite burden by 50% relative to a drug-free control chamber. We tested the xanthone series against amastigote-infected murine peritoneal macrophages. Macrophages were seeded into Labtek chamber slides (25,000 per well/8 chamber slide) and allowed to incubate overnight in Dulbecco's Modified Eagle Medium (DMEM) supplemental with 10% fetal calf serum. On the next day the cells were infected with *L. mexicana* promastigotes at an MOI of 5:1 and then incubated for 24 hours at 35° C. After incubation, the monolayers were washed with buffer and medium containing varying concentrations of each xanthone (0 to 10 μM) was added to each chamber. After 48 hours of incubation (i.e., Day 3 of the experiment) one set of slides was removed, fixed with methanol, and stained with Giemsa. For another set of slides, we replenished the culture medium, added fresh drug to each well as appropriate, and then incubated the chambers for another 48 hours before staining with Giemsa. $IC_{50}$ values were then averaged for 3 separate experiments and the results are presented in Table 4 and graphically in FIG. 7. The relative potency for each of the compounds observed on the $5^{th}$ day of the experiment was quite similar to the value obtained for 48 hours of drug exposure in the peritoneal macrophage system. The $IC_{50}$ values recorded for C5 and C6 exposure for 96 hours of treatment were 6 nM and 2 nM.

The strong correlation between hematin affinity and anti-leishmanial potency for the xanthone series is strong evidence that heme salvage is perturbed by the most active compounds. Furthermore, the remarkable potency of C5 and C6 (both diacidic weak bases) against intracellular amastigotes leads us to speculate that the drugs are acting by accumulating in the phagolysosome-as prescribed in the original design of this series. These nitrogenated xanthones have diethylaminoalkoxy groups extending from the 3 and 6 positions of the pharmacophore. So positioned, under mildly acidic conditions of pH such as those found in the digestive vacuole of the Plasmodium parasites or the phagolysosome of Leishmania infected macrophages, the positively charged ammonium cations align themselves in opposition to the propionate side chains of heme in a net-neutral electrostatic interaction yielding an especially stable heme: drug complex. Note that the charge nature of the drug that results on entry into acidic regions of the cell or parasite causes the drug to accumulate. It has not escaped our attention that the target of our drugs is immutable and that, in the case of the leishmania, the xanthones may not need to enter the parasite to cause its death (the drug merely needs to accumulate in the phagolysosome).

Other examples of specific Formula X compounds are illustrated below:

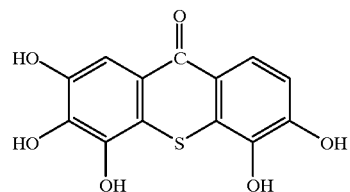

2,3,4,5,6-pentahydroxythioxanthone

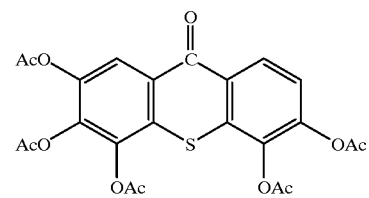

2,3,4,5,6-pentaacetoxythioxanthone

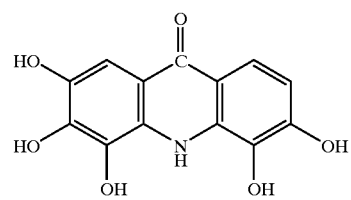

2,3,4,5,6-pentahydroxyacridone

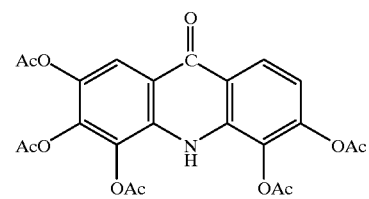

2,3,4,5,6-pentaacetoxyacridone

-continued
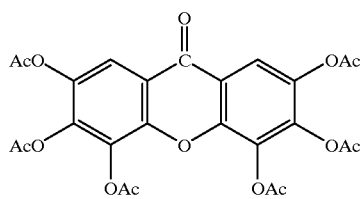
2,3,4,5,6,7-hexaacetoxyxanthone
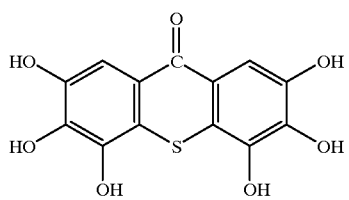
2,3,4,5,6,7-hexahydroxythioxanthone
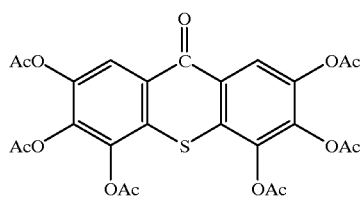
2,3,4,5,6,7-hexaacetoxythioxanthone
-continued
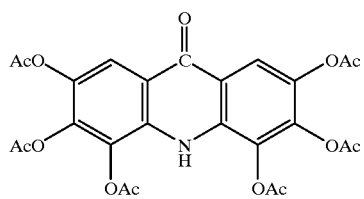
2,3,4,5,6,7-hexaacetoxyacridone
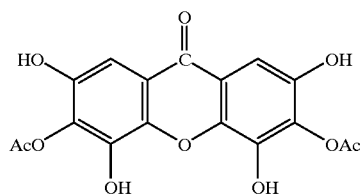
2,4,6,7-tetrahydroxy-3,6-acetoxyxanthone
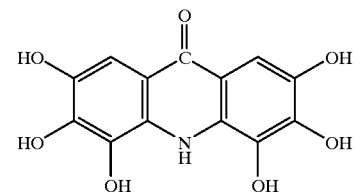
2,3,4,5,6,7-hexahydroxyacridone
TABLE 1
| Compound Name | Xanthone Structure | $IC_{50}$, $\mu M$ vs. Plasmodium |
|---|---|---|
| Xanthone |  | >10 |
| Mangostin |  | 5 |
| Mangiferin |  | 50 |

TABLE 1-continued
| Compound Name | Xanthone Structure | IC$_{50}$, μM vs. Plasmodium |
|---|---|---|
| 3,4,5,6,-Tetrahdroxy-xanthone | 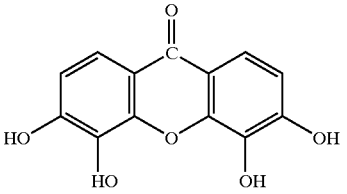 | 10 |
| 2,3,4,5,6-Pentahydroxy-xanthone | 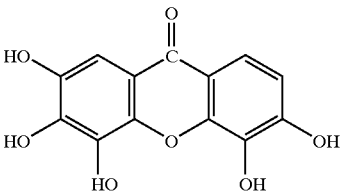 | 0.4 to 0.5 |
| 2,3,4,5,6,7-hexahydroxy-xanthone | 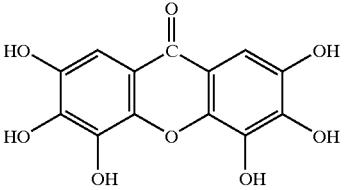 | 0.075 |
| 2,3,4,5,6-Pentamethoxy-xanthone | 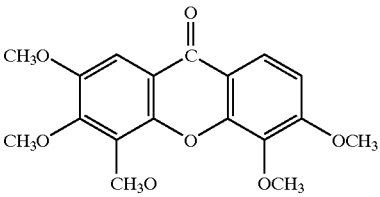 | >100 |
| 2,3,4,5,6-Penta-acetoxyxanthone | 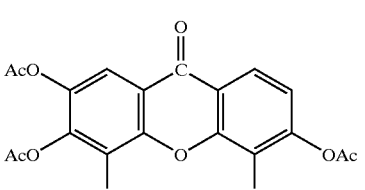 | 0.075 |
| 1,2,3,5,6,7-Hexahydroxy-xanthone | 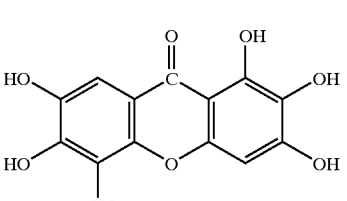 | 25–50 |
| 1,3-dihydroxyxanthone | 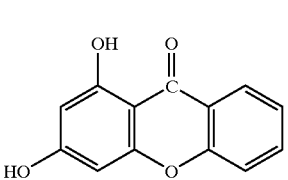 | >100 |

TABLE 1-continued
| Compound Name | Xanthone Structure | IC$_{50}$, μM vs. Plasmodium |
|---|---|---|
| 1,3,5,6,7-pentahydroxy-xanthone | 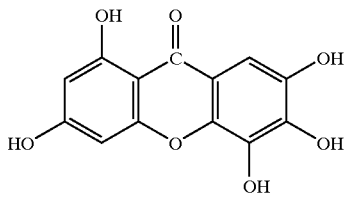 | 1 |
TABLE 2
| Chemical Name | Structure | IC$_{50}$ mg/ml for Leishmania |
|---|---|---|
| 2,3,4,5-penta-hydroxyxanthone "X %" | 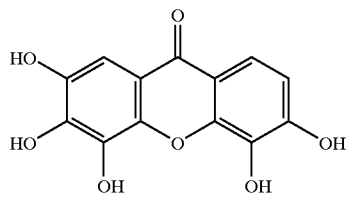 | 0.0015 |
| 2,3,4,5,6,7-hexa-hydroxyxanthone "X6" | 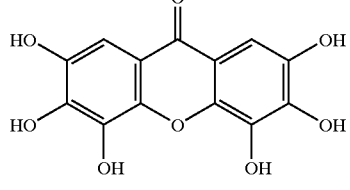 | 0.0015 |
| Mangostin | 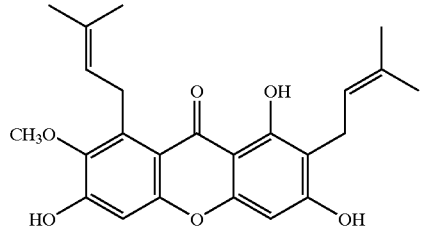 | 0.00041 |
| Mangiferin | 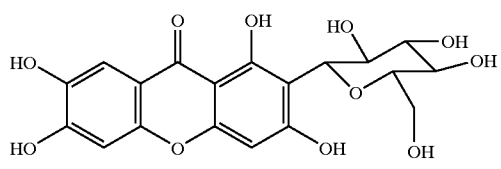 | >0.05 |
| Stibogluconate [Sodium Antimony (V) Gluconate] | 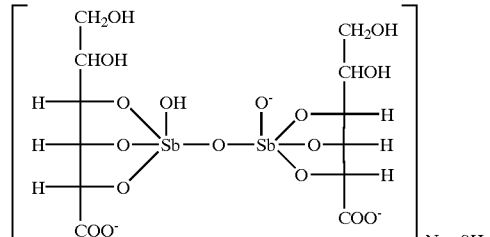 | 0.1 to 1.0 literature reported value |

TABLE 3
| Compound name | Compound structure | IC$_{50}$ μM, P. falciparum clone D6 | IC$_{50}$, μM in vitro heme polymerization |
|---|---|---|---|
| 2-hydroxyxanthone | 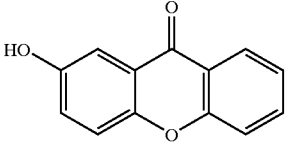 | 50 | >1000 |
| 3-hydroxyxanthone | 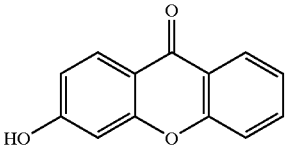 | >100 | >1000 |
| 1,3-dihydroxyxanthone | 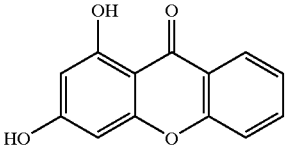 | 75 | >1000 |
| 3,6-dihydroxyxanthone | 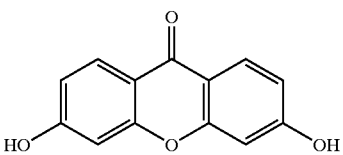 | >100 | >500 |
| 4,5-dihydroxyxanthone | 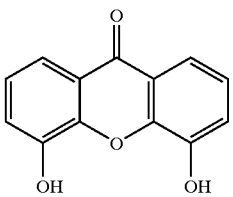 | 16 | 14 |
| 2,3,4-trihydroxyxanthone | 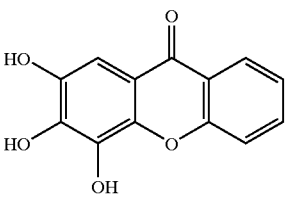 | 40 | 17 |
| 3,4,5,6-tetrahydroxyxanthone | 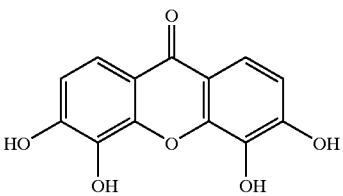 | 5 | 2.5 |
| 2,3,4,5,6-pentahydroxyxanthone (X5) | 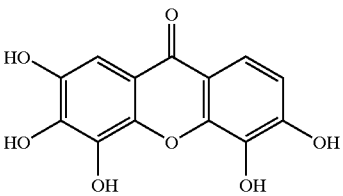 | 0.4 | 1.2 |

TABLE 3-continued

| Compound name | Compound structure | IC$_{50}$ µM, P. falciparum clone D6 | IC$_{50}$, µM in vitro heme polymerization |
| --- | --- | --- | --- |
| 1,3,5,6,7-pentahydroxyxanthone | (structure) | 1 | 9 |
| 2,3,4,5,6,7-hexahydroxyxanthone (X6) | (structure) | 0.1 | 1.4 |
| 2,3,4,5,6-pentamethoxyxanthone | (structure) | >100 | >1000 |
| 2,3,4,5,6-pentaacetylxanthone | (structure) | 0.075 | >1000 |

Table 4 provides antiparasitic activities for selected nitrogenated xanthones versus intraerythrocy *Plasmodium falciparum* (strain D6) and intracellular amastigotes of *Leishmania mexicana* M379. The xanthones illustrated in Table 4 typically included substituted alkyls, such as alkyl amines and alkoxyamines.

TABLE 4
| Chemical Name | Structure | IC$_{50}$ μM* P. falciparum D6 | IC$_{50}$ μM** L. mexicana |
|---|---|---|---|
| 3,6-bis-N,N-diethylamino-xanthone (36-DEAX) | 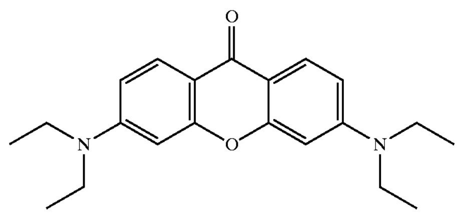 | 20 μM | not tested |
| 3,6-bis-β-(N,N-diethylamino)ethoxy-xanthone (36-DEAE-X) | 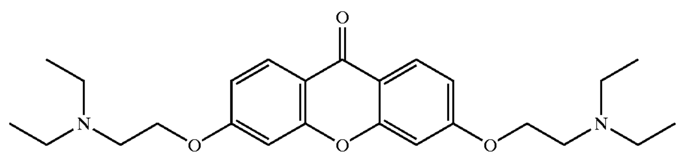 | 2.2 μM | ~1.25 μM |
| 3,6-bis-γ-(N,N-diethylamino)propoxy-xanthone (36-DEAP-X) | 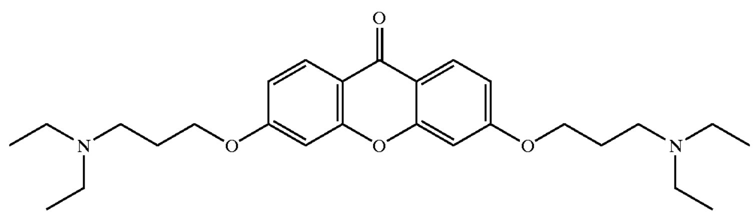 | 1.5 μM | 0.5 μM |
| 3,6-bis-δ-(N,N-diethylamino)butoxy-xanthone (36-DEAB-X) | 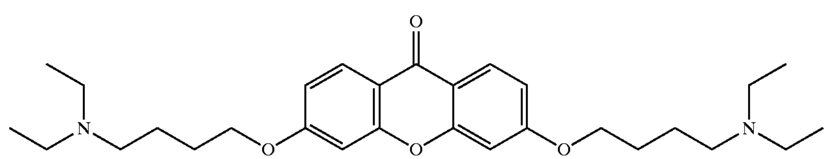 | 0.65 μM | 0.2 μM |
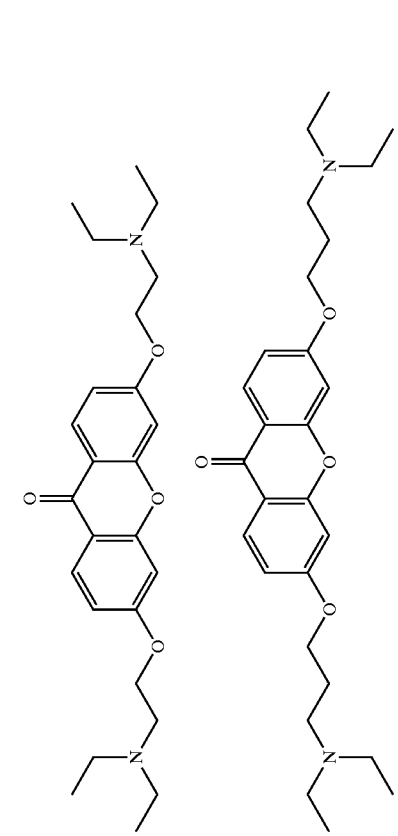

TABLE 4-continued

| Chemical Name | Structure | IC$_{50}$ μM* P. falciparum D6 | IC$_{50}$ μM** L. mexicana |
|---|---|---|---|
| 3,6-bis-ε-(N,N-diethylamino)-amyloxy-xanthone (36-DEAAmyl-X) C5 | | 0.10 μM | 0.06 μM |
| 3,6-bis-(N,N-diethylamino)-hexyloxy-xanthone (36-DEAHexyl-X) C6 | 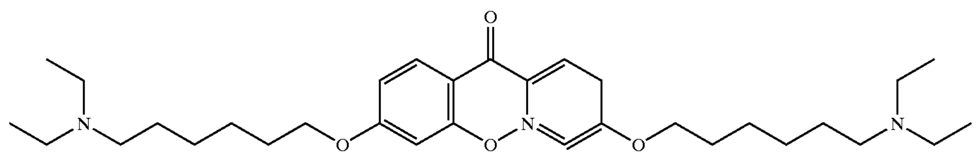 | 0.075 μM | 0.02 μM |
| 3,6-bis-(N,N-diethylamino)octyloxy-xanthone (36-DEAOctyloxy-X) C8 | 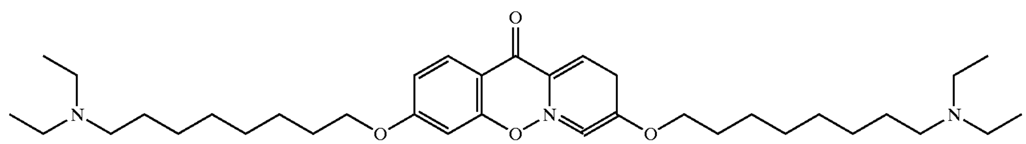 | 0.43 μM | Not tested |
| 4,5-bis-β-(N,N-diethylamino)ethoxy-xanthone (45-DEAE-X) | 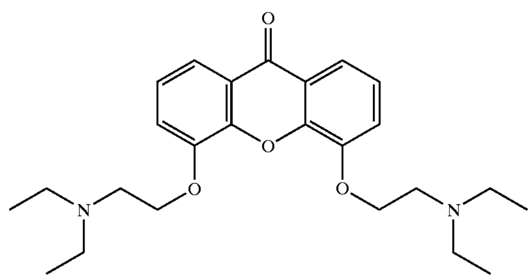 | 2.8 μM | not tested |

TABLE 4-continued

| Chemical Name | Structure | IC$_{50}$ μM* P. falciparum D6 | IC$_{50}$ μM** L. mexicana |
|---|---|---|---|
| 4,5-bis-β-(N,N-diethylamino)amyloxy-xanthone | 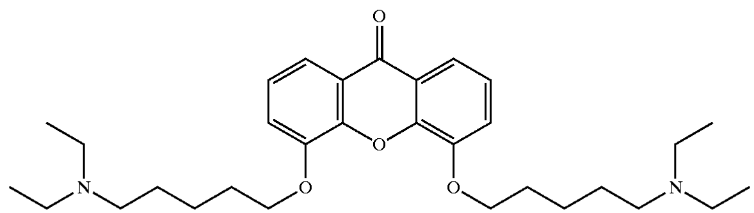 | 575 nM | not tested |
| 3,5-bis-(N,N-diethylamino)amyloxy-xanthone | 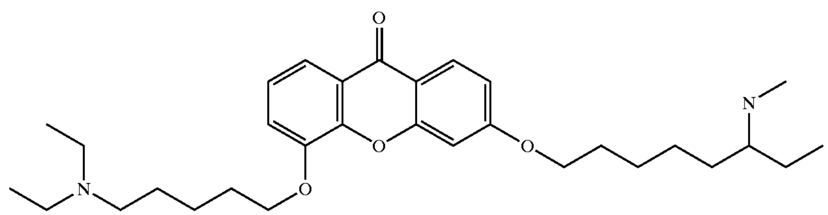 | 825 nM | Not tested |
| 3-(N,N-diethylamino)amyloxy-xanthone | 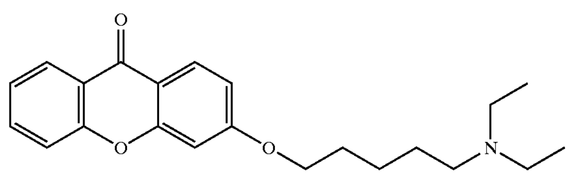 | 2.5 μM | Not tested |

*The data are the average of 2 experiments each performed in triplicate by the 72 hour assay. D6 is mefloquine resistant.
**The data are the results of 3 experiments in which bone-marrow-derived MOs were infected with L. Mexicana (MOI 10:1). 24 hours later, the medium was replaced and drug was added. After incubation for an additional 48 hours, the slides were fixed in methanol and stained with Giemsa. IC$_{50}$s reflect concentration required to reduce amastigote burden by 50% relative to drug-free controls (a minimum of 100 MOs were counted for each drug concentration).

VIII. Sources of Formula X1 Compounds and Preferred Method of Synthesis

Many xanthones and xanthone derivatives can be purchased commercially from sources including: ICN Biomedicals, Irvine, Calif., U.S.A.; Sigma Chemical Company, St. Louis, Mo., U.S.A.; Aldrich Chemical Company, Milwaukee, Wis., U.S.A.; and Janssen Chimica (Belgium). In addition, many xanthones are naturally occurring compounds which can be purified by methods such as those described in Hostettmann et al. (1995).

A. General Xanthone Synthesis Method

Xanthones according to the present invention may be synthesized by the general method described above, for the synthesis of 2,3,4,5,6,7-hexahydroxyxanthone and 2,3,4,5, 6-pentahydroxyxanthone. Essentially, this method comprises subjecting an o-hydroxy-o'-methoxy-benzophenone to base treatment (e.g., aqueous sodium hydroxide), which leads to the formation of the central oxygen-bridged ring; the o-phenoxide (from the o-hydroxyl in basic medium) then replaces the methoxide on the other ring by nucleophilic substitution. The net effect is expulsion of $CH_3O$—, and the formation of a diphenyl ether. Since the two phenyl rings are already linked by a carbonyl group, a xanthone is obtained. The o—OH,o'—$OCH_3$ groupings are required for this reaction; although the methyl could be replaced with other groups, this is not likely to be of any advantage since methyl ethers are readily available. However, other substituents can be present in the two aromatic rings of the benzophenones. For example, for the synthesis of the penta- and hexa-hydroxyxanthones described above, these other substituents were methoxy groups.

The benzophenones used in synthesizing the xanthones as described above may be obtained by combining substituted benzoic acids and methoxybenzenes by a condensation or other coupling procedure. In an exemplary condensation procedure, the benzoic acid carries an o-hydroxy group:

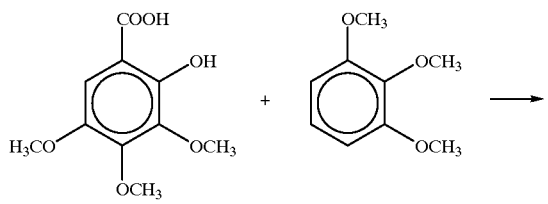

-continued

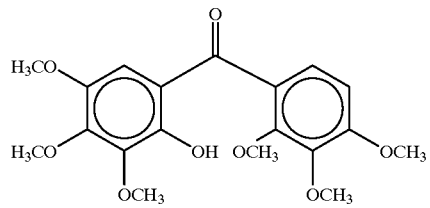

This coupling can be achieved by condensation in polyphosphoric acid or a mixture of phosphorus pentoxide and methanesulfonic acid. Alternatively, benzophenones may be synthesized by Friedel-Crafts acylation (of a benzoyl chloride and a polymethoxybenzene), or by the Hoesch synthesis, or by reaction of a benzoyl chloride with an appropriately metalated (e.g., lithiated) aromatic, or other methods.

In particular cases, additional substituents may be introduced into the benzophenone after the benzophenone has been synthesized.

Alternatively, xanthones may be derived from benzophenones by oxidative cyclization. This method essentially requires an o-hydroxy group on one ring and a free position (occupied by H) on the other ring. Oxidation (e.g., with $K_3[Fe(CN)_6]$, or $KMnO_4$) produces an oxygen bridge with the elimination of 2H.

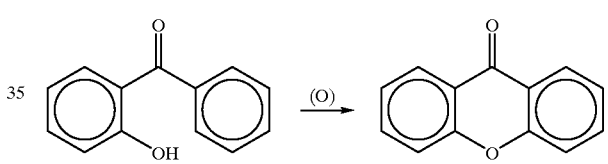

B. Synthesis of Thioxanthones

Thioxanthones may be obtained by a number of methods. Exemplary syntheses include: (1) combining an o-mercaptobenzoic acid with a halobenzene (preferably iodo or bromo); and (2) combining an o-halobenzoic acid (preferably either bromo or iodo) with a mercaptobenzene. The intermediate diphenylsulfide produced in each case is then condensed to yield the required thioxanthone as illustrated in the following schematic:

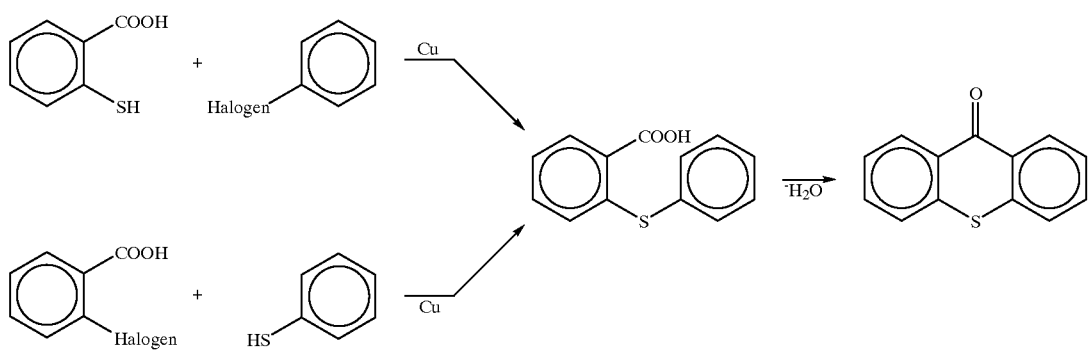

Methods of synthesizing thioxanthones using this general reaction scheme are described in Hollis-Showalter et al., *J. Med. Chem.*, 31, 1527 (1988).

C. Synthesis of Acridones

Acridones may be synthesized by a number of different methods. The following methods are exemplary and are well known in the art.

Acridones may be formed from o-nitrobenzophenones, which are reduced to obtain o-aminobenzophenones which are in turn cyclized with either o'-methoxy or o'-hydroxy groups to produce the acridones. The o-nitrobenzophenones which are used as starting materials may be obtained either by Friedel-Crafts acylation of phenols or methoxybenzenes using o-nitrobenzoylchlorides, or by direct nitration of benzophenones, or by coupling of lithiated arenes with o-nitrobenzol chlorides (e.g., as described by Parkham et al., *Journal of Organic Chemistry* 46, 1057 (1981). An exemplary synthesis is illustrated below:

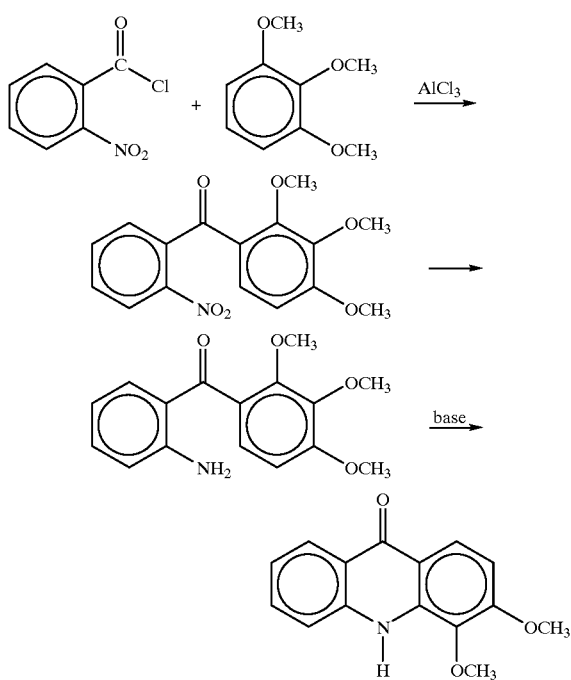

Alternatively, o-nitrobenzophenones may be formed by coupling of 2-methyl-3,1-benzoxazin-4-ones (from o-aminobenzoic acid by heating with acetic anhydride) with aromatic Grignard reagents (e.g., Adams et al. *J.C.S. Perkin Trans I* 2089 (1976)).

Alternatively, acridones may be produced by zinc chloride catalyzed condensation of hydroxyanthranilic acids and polyhydroxybenzenes (such as described by Bahar et al., *Phytochemistry* 21, 2729 (1982)) and illustrated in the following scheme:

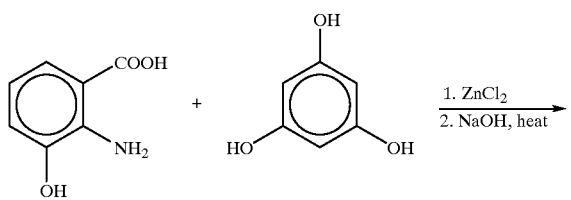

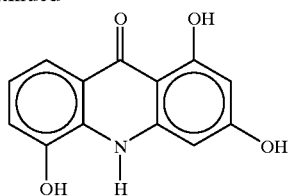

Acridones may also be formed by cycloaddition of derivatives of anthranilic acids with dehydrobenzenes such as described by Khanapure et al., *Tetrahedron Letters* 31:2869 (1990).

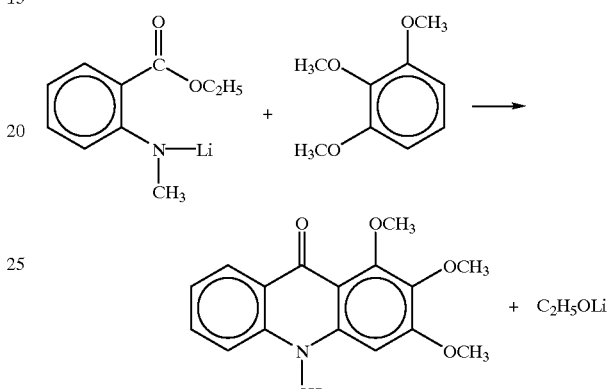

D. Deprotection

Deprotection of polymethoxyxanthones, polymethoxythioxanthones or polymethoxyacridones may be achieved in a number of ways, including treating with either hydriodic acid or with a methylene chloride solution of boron tribromide, and hydrolysis of the intermediate boron-phenoxy compound.

E. Synthesis of Alkoxyamine-Substituted Xanthones

A number of methods can be used to make alkoxyamine substituted xanthones. The first method comprises reacting a corresponding dihydroxyxanthone with an alkyl amine having a suitable leaving group, such as a halogen, in the presence of a base and typically with the addition of heat. Working embodiments of this general method have used chlorinated alkyl amines. These chlorinated alkyl amines were reacted with the corresponding hydroxyxanthones in an alcoholic solution in the presence of sodium hydroxide.

The second general method is a two step process. The first step involves reacting a corresponding hydroxyxanthone with an excess of an alkyl group having two leaving groups attached thereto, such as two halogens, e.g., 1,3-dibromoethane. This first step generally is conducted in acetonic solvent with a carbonate base, such as potassium carbonate. The resulting halogenated ethers are then reacted with an appropriate amine, such as diethyl amine, to displace the second halogen leaving group and form the alkoxyamine-substituted xanthones. The second step has been done in an ether solvent, such as tetrahydrofuran. Heat can be used to increase reaction rate and/or yield of both steps.

F. Replacing Carbonyl Oxygen with Sulfur to Form Thiocarbonyls

Formula X indicates that the Y group can be either oxygen or sulfur, i.e., thiocarbonyls. Thiocarbonyl can be made from the corresponding ketones using a number of reagents, including without limitation, Lawesson's reagent [see, Lawesson et al. *Bull. Soc. Chim. Belges* 87:223 (1978); Lawesson et al. *Bull. Soc. Chim. Belges* 87:229 (1978); Lawesson et al. *Bull. Soc. Chim. Belges* 87:293 (1978)], 2,4-bis(4-methoxyphenyl)-1,2,3,4-dithiadiphosphonate-2,4-disulfide, bis(tricyclophexyltin)-sulfide [$(R_3Sn)_2S$, where R=cycolhexyl] or $P_4S_{10}$.

IX. Activity of Formula X Compounds

The Formula X compounds according to the present invention are useful in inhibiting the growth of microbial pathogens, including protozoan parasites (for example, Plasmodium sp. and Leishmania sp.) and yeast (for example, *Candida albicans*). Thus, one aspect of the present invention is a method of inhibiting the growth of a microbial pathogen by contacting the microbial pathogen with a Formula X compound. In this context, it is, of course, necessary to contact the microbial pathogen with a sufficient amount of the Formula X compound to inhibit growth of the pathogen. One skilled in the art will readily appreciate that the amount of compound sufficient to inhibit the growth of the microbial pathogen will vary according to the Formula X compounds selected, the target microbial pathogen and the environment in which the microbial pathogen is growing. Standard methods are available for determining the $IC_{50}$ concentration of Formula X1 compounds for microbial pathogens in vitro. Alternatively, $ED_{50}$ values may be determined in an animal. See Munson, Principles of Pharmacology (Chapman and Hall, 1995) Chapter 1. Exemplary $IC_{50}$ values (showing activities against Plasmodium and Leishmania, respectively) are presented in Tables 1 and 2 of U.S. Pat. No. 5,977,077, and Table 3 above These values relate to the inhibition of a microbial pathogen grown in vitro. Contacting the microbial pathogen with a compound according to Formula X1 may also be performed in vivo where necessary to inhibit the growth of microbial pathogens under physiological conditions. The "Pharmaceutical Compositions" section below addresses compositions and dosages appropriate for inhibiting the growth of microbial pathogens in such circumstances.

X. Heme Polymerization and Formula X Compounds

Figure 2:
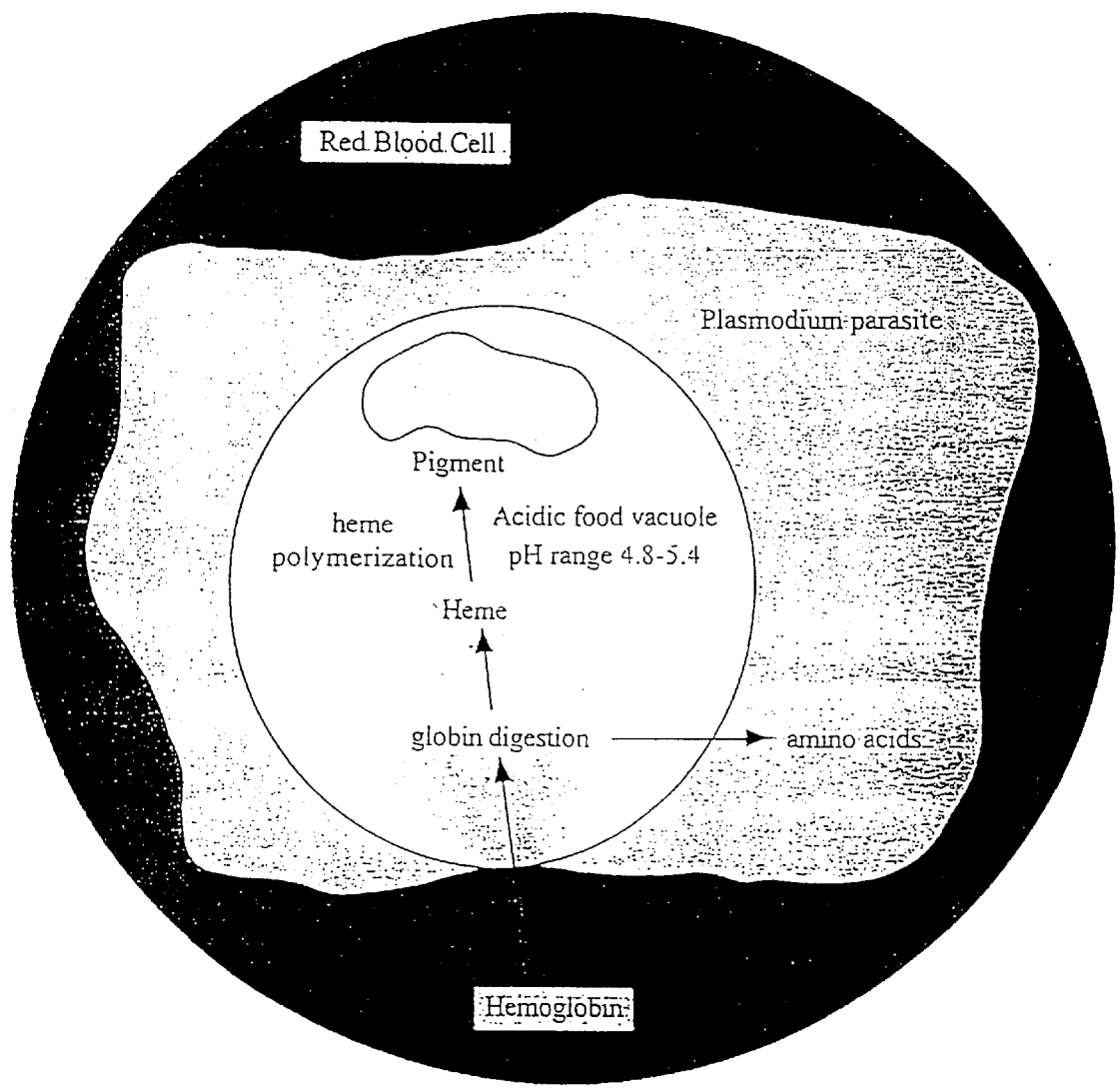
FIG. 2 is a schematic depiction of hemoglobin digestion (with the concomitant release of heme) by the intracellular parasite Plasmodium falciparum.

Certain parasites, including Plasmodium spp. and Schistosoma spp., obtain amino acids for growth by degrading hemoglobin from the red blood cells of the infected host. In the case of the malarial parasite, degradation of hemoglobin takes place in the parasite's digestive vacuole, which is an acidic proteolytic compartment essential to the metabolism of the parasite (see FIG. 2). As the hemoglobin is broken down, free toxic heme is released. To prevent the build-up of toxic heme, the parasites polymerize the heme for storage in a non-toxic form called hemozoin.

While the Formula X compounds of the present invention exhibit anti-microbial activity against a range of pathogens, it has now been discovered that a certain sub-group of these compounds form complexes with free heme, which results in the inhibition of heme aggregation. In turn, this leads to the accumulation of toxic heme in the parasite's digestive vacuole and ultimately to the death of the parasite. These compounds include those listed in Table 3 belong to a group related to Formula X compounds which are referred to herein as "Formula XH compounds". Formula XE compounds may be particularly effective against those parasites, including Plasmodium and Schistosoma, which rely on hemoglobin catabolism to survive in the infected host or must rely on the host's heme iron reserves for synthesis of critical ferroproteins.

Figure 3:
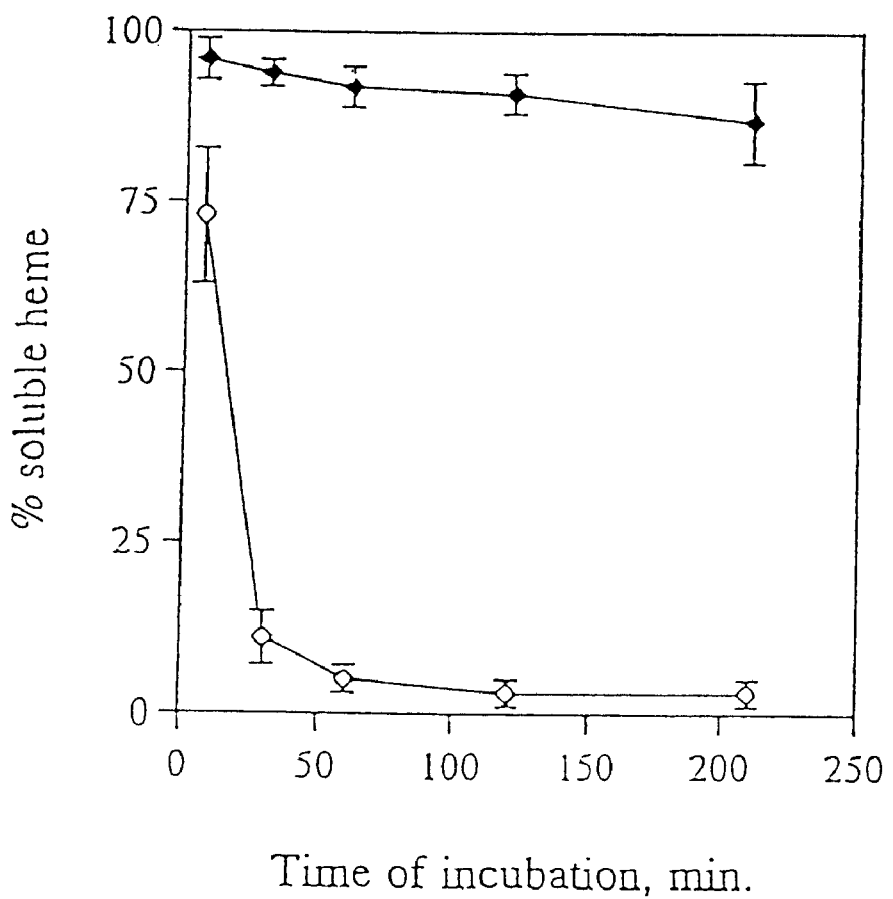
FIG. 3 is a graph showing the inhibition of in vitro heme aggregation by compound X5 (A=O) (2,3,4,5,6-pentahydroxyxanthone). Heme and X5 (A=O) concentrations were 25 μM. Open diamonds indicate heme alone (control), filled diamonds represent heme and X5 (A=O) together.

Table 3 below shows the ability of a range of formula X1 compounds to inhibit heme aggregation, as determined using the simple in vitro heme aggregation assay described above. Under the conditions of this assay, heme aggregation was found to be pH dependent (polymerization required a pH of between 4.5 and 5.5). Aggregation occurred spontaneously and was more than 95% complete within 2 hours of commencement of incubation with the compound X5 (A=O)(see FIG. 3).

The $IC_{50}$ values shown in Table 3 are the average of at least two independent determinations of full dose-response curves. Xanthone and the tested monohydroxyxanthones did not exhibit any inhibitory activity in this assay. Moderate inhibitory activity (i.e., $IC_{50}$ 8–20 μM) was observed for the compounds bearing a single hydroxy group at either 4-or 5-position, whereas the greatest activity was observed for xanthones containing hydroxy groups at both positions. For example, 2,3,4-trihydroxyxanthone exhibited an $IC_{50}$ of 16.5 μM, while 2,3,4,5,6-pentahydroxyxanthone (X5, A=O) yielded a value of 1.2 μM. Consistent with this structure-activity profile, the 4,5-hydroxylated xanthones also exhibited the most pronounced in vitro antimalarial activity. Furthermore, pentamethoxy-X5 and pentaacetyl-X5 were inactive in this assay, though the latter was shown to be a potent antimalarial agent. Presumably, pentaacetyl-X5 is hydrolysable in infected red blood cells by a non-specific esterase, whereas pentamethoxy-X5 is not.

Figure 4:
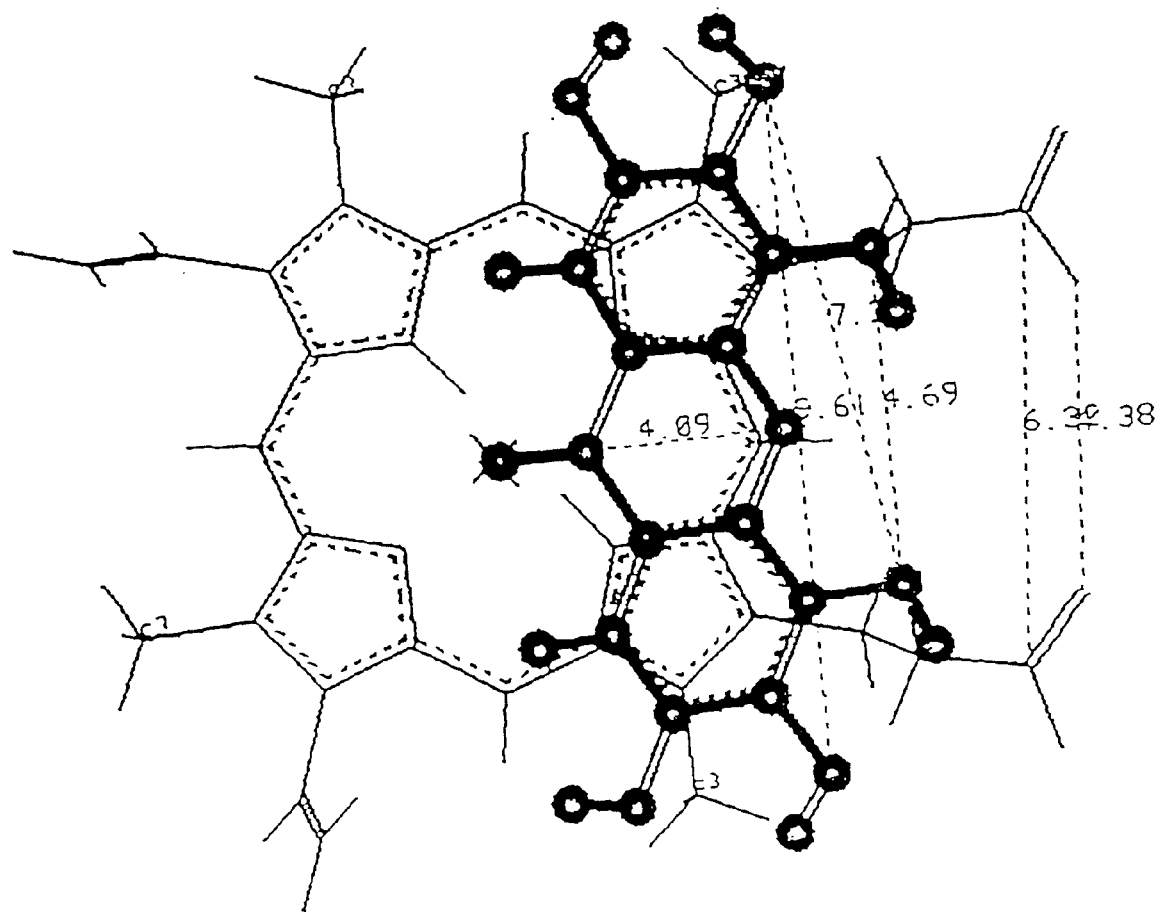
FIG. 4 is a computer simulation of compound X6 (A=O) (2,3,4,5,6,7-hexahydroxyxanthone) complexing with free heme.
Figure 5:
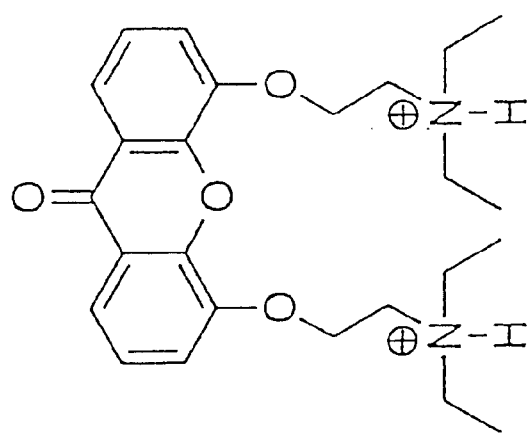
FIG. 5. provides the structure of 45-DEAE-X [4,5-bis-(β-diethylamino-ethoxy)-xanthone] and formation of the diprotonated form upon entry of this compound into the parasite digestive vacuole.
Figure 5:
Figure 5:
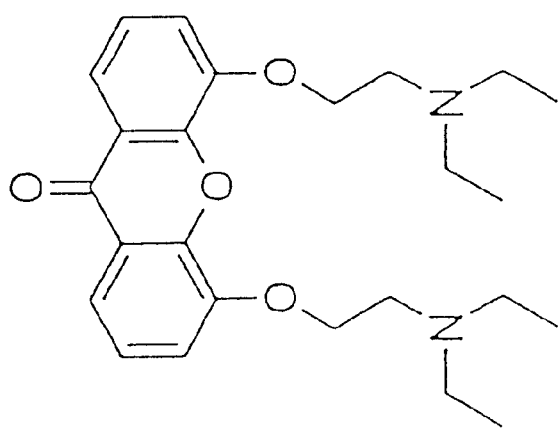

These findings suggest that X5 (A=O) and other compounds shown in Table 3 form soluble complexes with heme monomers or oligomers and interfere with hemozoin formation. Such action may result in the death of the parasite by one of several mechanisms, including preventing detoxification of free heme, starving the parasite for iron, or increasing the osmotic pressure within the parasite digestive vacuole. The relative abilities of these compounds to inhibit in vitro heme polymerization are in good correlation with their in vitro antimalarial activities, and are indicative of the following structure-activity relationships: (I) in general, a higher degree of hydroxylation is favored for the inhibitory activity; and (ii) hydroxylation in the lower half of the pharmacophore may be central to full activity. Based on these observations, a model for the interaction of these compounds is presented in FIG. 4. This model shows the interaction of X6 (A=O) with heme and serves to illustrate the following interactions: (1) between the heme iron and the carbonyl oxygen; (2) between the two planar aromatic systems; and (3) between the carboxylate side groups of the heme and the 4-and 5-position hydroxyls of the xanthone. These interactions may take any form of known chemical interaction, including covalent bonding, hydrogen bonding, ionic bonding, and polar and nonpolar bonding. Moreover, this model predicts that chemical modifications at the 3, 4, 5 or 6 positions which improve association with the heme carboxylate groups will result in even greater antimalarial activity.

Accordingly, Formula XH compounds can be defined as compounds which inhibit heme polymerization and which have the following structure

where X is a group capable of interacting with the iron atom in heme; Y is a substantially planar aromatic system capable of interacting with the porphyrin ring of heme, possibly through overlapping pi—pi orbitals; and Z represents one or more groups capable of interacting with at least one carboxylate side group of heme.

In preferred embodiments, a Formula XH compound has the following structure:

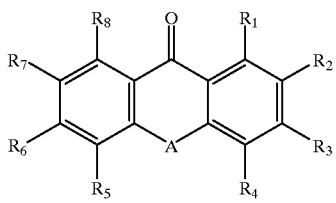

where A is oxygen, substituted antimony (stibium), sulfur or N-R' wherein R' is H, OH, alkyl, haloalkyl, preferably lower alkyl or lower haloalkyl wherein "lower" means 10 or fewer carbon atoms, aryl or haloaryl; $R_1$—$R_8$ are independently selected from the group consisting of H, OH, halogen, aryl, arylamine, alkyl, substituted alkyl (such as alkylamine, alkylthio and haloakyl, and alkyl groups having two or more such substituents), alkoxy, substituted alkoxy (such as alkoxyamine, alkoxythio and haloalkoxy, and alkoxy groups having two or more such substituents) amino, ester and nitro groups and O-linked and C-linked carbohydrates. Preferably, at least one member of the $R_3/R_6$ or $R_4/R_5$ substituent pairs, and even more preferably both members of the pair, is selected from the group consisting of amino, substituted amino, alkylamino, substituted alkyl amino, arylamino, amidinium, alkylamidinium, guanidinium, alkylguanidinium, hydroxy, alkylhydroxy, alkoxyhydroxy, alkoxyamine, cycloalkoxyamine, alkoxy-substituted amine, azido, carboxylic esters of hydroxy, alkylhydroxy and alkoxyhydroxy groups, COOH, alkyl—COOH, $CONH_2$ and alkyl—$CONH_2$. The other member of the $R_3/R_6$ and $R_4/R_5$ substituent pair is selected from the group consisting of H, OH, halogen, aryl, arylamine, alkyl, substituted alkyl (such as alkoxy, alkylamine, alkylthio and haloakyl), amino, substituted amino, ester and nitro groups, O-linked and C-linked carbohydrates, alkylamino, substituted alkyl amino, arylamino, amidinium, alkylamidinium, guanidinium, alkylguanidinium, alkylhydroxy, alkoxyhydroxy, alkoxyamine, alkoxy-substituted amine, azido, carboxylic esters of hydroxy, alkylhydroxy and alkoxyhydroxy groups, COOH, alkyl—COOH, $CONH_2$ and alkyl—$CONH_2$.

Examples of Formula XH compounds include, without limitation, 4,5-dihydroxyxanthone, 2,3,4-trihydroxyxanthone, 3,4,5,6-tetrahydroxyxanthone, 2,3,4,5,6-pentahydroxyxanthone, 1,3,5,6,7-pentahydroxyxanthone, 2,3,4,5,6,7-hexahydroxyxanthone, 3,6-bis-N,N-diethylaminoxanthone, 3,6-bis-β-(N,N-diethylamino)ethoxyxanthone, 3,6-his-γ-(N,N-diethylamino)propoxyxanthone, 3,6-bis-δ-(N,N-diethylamino)butoxyxanthone, 3,6-bis-ε-(N,N-diethylamino)amyloxyxanthone, 3,6-bis-ζ-(N,N-diethylamino)hexyloxyxanthone, 3,6-bis-η-(N,N-diethylamino)heptyloxyxanthone, 3,6-bis-θ-(N,N-diethylamino)octyloxyxanthone, 3,6-bis-ι-(N,N-diethylamino)nonyloxyxanthone, 3,6-bis-κ-(N,N-diethylamino)decyloxyxanthone, 4,5 bis substituted amines and alkoxyamine analogs, such as 4,5-bis-N,N-diethylaminoxanthone, 4,5-bis-β-(N,N-diethylamino)ethoxyxanthone, 4,5-bis-γ-(N,N-diethylamino)propoxyxanthone, 4,5-bis-δ-(N,N-diethylamino)butoxyxanthone, 4,5-bis-ε-(N,N-diethylamino)amyloxyxanthone, 4,5-bis-ζ-(N,N-diethylamino)hexyloxyxanthone, 4,5-bis-η-(N,N-diethylamino)heptyloxyxanthone, 4,5-bis-θ-(N,N-diethylamino)octyloxyxanthone, 4,5-bis-ι-(N,N-diethylamino)nonyloxyxanthone, and 4,5-bis-κ-(N,N-diethylamino)decyloxyxanthone.

Methods of synthesizing these compounds are known in the art and are described in a representative manner above in relation to Formula X compounds. Additional detail concerning the synthesis of compounds satisfying Formula X are provided below in the examples.

Based on empirical results and the mechanism proposed for the interaction of Formula XH compounds with heme, the 3,6 and 4,5-bis-substituted alkylamine and alkoxyatnine compounds appear particularly effective in complexing with heme. 4,5-bis-(N,N-diethylamino)ethoxyxanthone is a diprotic base, which upon entry into the acidic vacuole becomes positively charged, effectively "trapping" the drug within this compartment where it will complex with heme. The positively charged residues are arranged to be in opposition to the heme carboxylate side chains so as to facilitate formation of a soluble heme:xanthone complex (the ionic nature of the trapped xanthone will also maintain the drug:heme complex in solution). 4,5-DEAE-X may be readily prepared from 4,5-dihydroxyxanthone (which as described above, is synthesized by base-catalyzed cyclization of the appropriate ortho-hydroxy-methoxylated-benzophenone). To produce 4,5-DEAE-X, 4,5-Dihydroxyxanthone was reacted under basic conditions with ethylene dibromide to yield 4,5-bis-(β-bromoethoxy)-xanthone. The latter was then reacted with diethylamine to yield the desired product.

The present invention thus encompasses the use of Formula XH compounds to inhibit heme polymerization and to inhibit the growth of those pathogens which polymerize heme, such as Plasmodium. It also is apparent that the Formula XH compounds may be used to treat infections caused by pathogens which require access to the host heme iron reserves for survival.

XI. Pharmaceutical Compositions

Formula X and XH compounds having anti-microbial activity are administered to patients in conventional dosage forms prepared by combining an appropriate dose of the compound with standard pharmaceutical carriers. Suitable pharmaceutical carriers may be, for example, solids or liquids. Suitable solid carriers include lactose, magnesium stearate, terra alba, sucrose, talc, stearic acid, gelatin, agar, pectin, acacia and cocoa butter. The amount of solid carrier will vary widely depending on which carrier is selected, but preferably will be from about 25 mg to about 1 gram. Suitable liquid carriers include syrup, peanut oil, olive oil, sesame oil, propylene glycol, polyethylene glycol and water. The carrier or diluent may also include time delay material well known to the art such as, for example, glyceryl, monostearate or glycerol distearate, either alone or with a wax. The foregoing examples of suitable pharmaceutical carriers are only exemplary and one of skill in the art will recognize that a very wide range of such carriers may be employed.

The formulation of the Formula X and XH compounds with a pharmaceutical carrier can take many forms. For example, the formulation may be a tablet, capsule, powder, suppository, lozenge, syrup, emulsion, liquid suspension or solution, or sterile injectable liquid. The pharmaceutical compositions are prepared by conventional techniques involving procedures such as mixing, granulating and compressing, and dissolving the ingredients. As will be appreciated from the foregoing exemplary formulations, administration of the compounds can be by any known route, including oral administration, intramuscular and intravascular injection.

The methods of treating a patient suffering from a microbial disease, such as malaria, in accordance with this invention comprise administering to the patient a therapeutically effective amount of a compound according to Formula X or Formula XH. Preferably, the patient will be administered the compound in a formulation as described above (i.e. in combination with a pharmaceutical carrier), the formulation having a therapeutically effective amount of the compound. As used herein, "a therapeutically effective amount" preferably is an amount that results in complete remission of the disease. However, it will be recognized that any improvement in the patient's condition is clinically advantageous. Hence, "a therapeutically effective amount" also encompasses amounts of the administered compound that result in partial remission of the disease or which slow or limit the further progression of the disease, or which inhibit the growth of the infectious agent or which reduce the clinical signs and symptoms of the disease (for example, fever and chills in a malaria infection). It is anticipated that therapeutically effective dosages which slow or limit the spread of the disease, or which inhibit the growth of the parasite will be particularly suitable for combination with other anti-microbial drugs.

The compounds of the invention can be administered in a daily dosage schedule of from about 10 mg to about 10 g. One skilled in the art will recognize that in determining the active amount of the anti-microbial compound to be administered, the activity of the specific compound selection, the age, weight and condition of the patient and the administration of other drugs to the patient should be considered.

The Formula X and XH compounds also may be indirectly provided to patients in pro-drug formulations. For example, Formula X and XH xanthones may be produced by co-administration of an oxidant agent with a corresponding substituted benzophenone under physiological conditions. A pro-drug is thus defined herein as a compound which reacts under physiological conditions to produce a Formula X or XH compound. Thus, the pro-drug for 4,5-DEAE-X would be 3,3'-bis-(β-diethylamino)ethoxy-2-hydroxy-benzophenone, and the pro-drug for 2,3,4,5,6-pentahydroxyxanthone would be 2,3,3',4,4',5'-hexahydroxybenzophenone (exifone). The provision of the X and XH compounds in pro-drug form (i.e. the corresponding benzophenones) may be particularly useful where the oxidant agent which is administered with the pro-drug is another anti-microbial agent. For example, the widely used anti-malarial agent primaquine is such an oxidant agent, and the combination of an XH pro-drug with primaquine is expected to be a particularly efficacious treatment for malaria.

EXAMPLES

The following examples are provided to illustrate certain features of the present invention. These examples should be considered illustrative only. The scope of the present invention should be determined not by reference to the following examples, but rather by reference to the attached claims.

Example 1

This example describes the synthesis of 3,6-bis-β-(N,N-diethylamino)ethoxy-xanthone by the first general method described above. 0.30 gram of 3,6-dihydroxyxanthone [See, R. Meyer et al., *Ber.*, 30:989 (1897)] and 1.1 grams of NaOH were combined in an alcoholic solvent and warmed. 2.0 grams of $(C_2H_5)_2NCH_2CH_2Cl \cdot HCl$ were added to the mixture, and the mixture was then heated to reflux for forty minutes. Thereafter, another 4 grams of NaOH and 8 grams of $(C_2H_5)_2NCH_2CH_2Cl \cdot HCl$ were added to the refluxing mixture. After standing overnight, the mixture was poured into water (about 400 milliliters) and extracted twice with methylene chloride (100 milliliters; 50 milliliters). The combined methylene chloride extracts were extracted with 250 milliliters of 8% HCl. The resulting aqueous phase was again extracted with methylene chloride (2×50 milliliters). The aqueous phase was combined with 200 milliliters of 5N NaOH and extracted with ether (3×75 milliliters). The combined organic extracts were evaporated at room temperature to provide 0.39 grams of substantially pure, colorless crystals of 3,6-his-β-(N,N-diethylamino) ethoxyxanthone (70%).

The crude product was purified using silica gel chromatography. The silica gel was wetted with methylene chloride and the sample placed on the column using methylene chloride. The column was then flushed with 100 milliliters of hexanes. The compounds were eluted with triethylamine and hexanes (1:1). After evaporation, 0.23 gram of a product pure by TLC and proton NMR was obtained. The product obtained had an Rf of about 0.4.

3,6-bis-γ-(N,N-diethylamino)propoxyxanthone, 4,5-bis-β-(N,N-diethylamino)ethoxyxanthone, and 4,5-bis-γ-(N,N-diethylamino)propoxyxanthone have been made in a manner substantially identical to that described in Example 1. γ-N,N-diethylamino-1-chloropropane was made according to the method described by A. Marxer, *Helvetica Chimica Acta*, 24:709 (1941). Substituted xanthones having more than three methylene units in the alkoxyamine side chain are difficult to make according to this first method in view of competing side reactions that occur with the halogenated amine reagent.

Example 2

This example described the synthesis of 3,6-bis-ε(N,N-diethylamino)pentyloxy-xanthone. 0.30 gram of 3,6-dihydroxyxanthone, 5.16 grams of 1,ω-dibromopentane, 50.0 milliliters of acetone and 5.0 grams of potassium carbonate were heated with stirring for eight hours. After cooling, the mixture was vacuum filtered and the solvent and excess dibromopentane were removed. The resulting solid was recrystallized from aqueous acetone to provide 0.80 gram of substantially pure product (about an 87% yield). This product was then used without further purification in the next step.

3,6-bis-(ω-bromopentoxy)xanthone, 5.0 milliliters of anhydrous tetrahydrofuran and 11 milliliters of diethylamine were refulxed for 12 hours. After cooling, precipitated material was filtered off and the filtrate evaporated using a stream of air. The crude product was then purified using silica-gel chromatography. The silica was wetted with methylene chloride, and the sample transferred to the column, using methylene chloride. The column was first flushed with 350 milliliters of methylene chloride, second with 110 milliliters of hexane to displace the methylene chloride, and the compound was eluted with a 1:1 triethylamine:hexane mixture.

The compound so obtained was then converted to the hydrochloride salt. 0.34 gram of the compound was dissolved in 10 milliliters of methanol. The mixture was then placed in an ice bath, and gaseous hydrochloric acid was then introduced for seven minutes with stirring. The brightly yellow solution was set aside to air dry. After about 24 hours, a yellow oil was obtained, which was placed under vacuum to provide 0.399 gram of the hydrochloride salt.

The present invention has been described with reference to certain preferred embodiments. It will be appreciated that the scope of the invention can be broader than that described. For example, certain alkoxydiethylamine xanthones are described. A person of ordinary skill in the art will realize that additional amines are within the scope of the present invention, such as alkoxydipropylamine xanthone, cycloalkylamines, such as dicyclopropyl amine, or cycloalkylimines, such as pyrrolidine. The true scope of the present invention therefore should be determined with reference to the following claims.

REFERENCES

Atamna, H., and H. Ginsburg (1993), Origin of reactive oxygen species in erythrocytes infected with *Plasmodium falciparum* [published erratum appears in *Mol. Biochem. Parasitol.* (1994) 63:312], *Mol. Biochem. Parasitol.* 61:231–41.

Aust, S., M. LA, and C. Thomas (1985), Role of metals in oxygen radical reactions. *Journal of Free Radicals in Biology and Medicine* 1:3–25.

Brodie, B., J. Axelrod, P. Shore, and S. Udenfriend (1954), Ascorbic acid in aromatic hydroxylation. II. Products formed by reaction of substrates with ascorbic acid, ferrous ion, and oxygen, *J. Biological Chemistry* 208:741–749.

Campbell, W. (1986), The chemotherapy of parasitic infections, *J. Parasitol.*, 72:45–61.

Cooper et al. (1992) *J. of Antibiotics* 45:444–453.

Cowman, A. F. and S. J. Foote (1990), Chemotherapy and drug resistance in malaria, *Int. J. Parasitol.*, 20:503–13.

Elabbadi, N., M. Ancelin, and H. Vial (1992), Use of radioactive ethanolantine incorporation into phospholipids to assess in vitro antimalarial activity by the semiautomated microdilution technique. *Antimicrob. Agents Chemother.*, 36:50–55.

Ghosal et al. (1978) *J. Pharm. Sci.* 67:721–722.

Goldstein, D., D. Meyerstein, and G. Czapski (1993), The Fenton Reagents. *Free Radical Biology and Medicine* 15:435–445.

Grogl, et al. (1992) *Am. J. Trop. Med. Hyg.* 47:117–126.

Grover, P., G. Shah, and R. Shah (1955), *J. Chem. Soc.*:3982 and Grover, P., G. Shah, and R. Shah (1956), Xanthones: Part V-A new synthesis of Lichexanthone. 15B. *J. Sci. Indust. Res.* 629–633.

Hambloch and Frahm (1984) *Eur. J. Med. Chem.—Chim. Ter.* 20:71–77.

Heyneman, D. (1988), The Worldwide Burden of Parasitic Disease, in *Parasitic Infections,* J. Leech, Hostettmann et al. (1995) in *Phytochemistry of Plants Used In Traditional Medicine*, chapter 2, (Hostettmann et al. ed) Oxford Science Publications. M. Sande and R. Root, Eds. Churchill Livingstone: New York. pp. 11–32.

Larrey, D. (1989), Exifone: a new hepatotoxic drug, *Gastroenterol. Clin. Biol.*, 13:333–334.

Maissant, J., C. Bouchoule, P. Canesson, and M. Blanchard (1983), Hydroxylation des composés aromatiques par le systeme d'Udenfriend: Remplacement de l'acide ascorbique par une réduction électrochimique, *Journal of Molecular Catalysis* 18:189–192.

Mayer and Fikentscher (1956) *Chem. Ber.* 89:511.

Mebrahtu, Y., P. Lawyer, J. Githure, J. B. Were, R. Muigai, L. Hendricks, J. Leeuwenburg, D. Koech, and C. Roberts (1989), Visceral leishmaniasis unresponsive to pentostam caused by *Leishmania tropica* in Kenya. *Am. J. Trop. Med. Hyg.*, 41:289–94.

Olliaro and Goldberg (1995) *Parasitology Today,* 11:294–297.

Sultanbawa (1980) *Tetrahedron* 36:1465–1506.

Trager and Jensen (1976) *Science* 193:673–675.

Udenfriend, S., C. Clark, J. Axelrod, and B. Brodie (1954), Ascorbic acid in aromatic hydroxylation. I. A model system for aromatic hydroxylation, *J. Biol. Chemistry* 208:731–739.

Vossen, et al. (1993) *Lipids* 28, 857–861.

Wang and Liu (1994) *J. Natural Products* 57:211–217.

Winter et al. (1996) *Antimicrob. Agents Chemother.* 40:1408–1411.

World Health Organization (1991), United Nations Development Program/WorldBank/WHO Special Programme for Research and Training in Tropical Diseases. Tropical diseases: progress in research, 1989–1990:29–40.

What is claimed is:

1. A compound according to Formula X

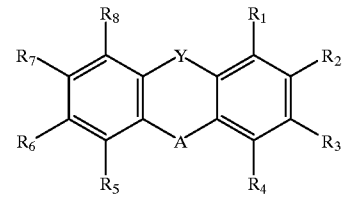

Formula X where A is oxygen or sulfur; $R_1$–$R_2$, $R_4$–$R_5$, and $R_7$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; at least one of $R_3$ and $R_6$ is independently selected from the group consisting of amino, substituted amino, alkylamino, substituted alkyl amino, arylamino, amidinium, alkylamidinium, guanidinium, alkylguanidinium, alkylhydroxy, alkoxyhydroxy, alkoxyamine, alkoxy-substituted amine, and azido groups, COOH, alkyl-COOH, $CONH_2$ and alkyl-$CONH_2$ with the other of $R_3$ and $R_6$ selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; and Y is selected from the group consisting of C=O, CH—OH, S=O, and $SO_2$.

2. The compound according to claim 1 where Y is S=O.

3. The compound according to claim 1 where A is sulfur.

4. The compound according to claim 1 where Y is carbonyl.

5. The compound according to claim 1 where A is oxygen.

6. The compound according to claim 1 where A is oxygen and Y is carbonyl.

7. The compound according to claim 6 where at least one of $R_3$–$R_6$ is dialkylaminoalkoxy.

8. The compound according to claim 6 where two or more of $R_3$–$R_6$ are alkoxyamines.

9. A composition comprising a pharmaceutical carrier and a compound having Formula X

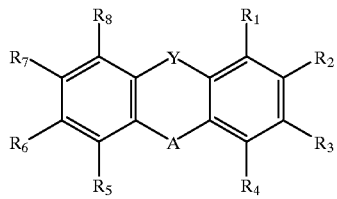

Formula X

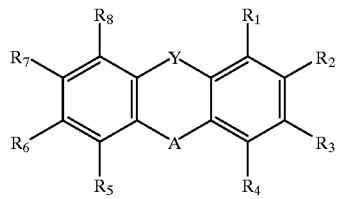

Formula X where A is oxygen or sulfur; $R_1$–$R_2$, $R_4$–$R_5$, and $R_7$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; at least one of $R_3$ and $R_6$ is independently selected from the group consisting of amino, substituted amino, alkylamino, substituted alkyl amino, arylamino, amidinium, alkylamidinium, guanidinium, alkylguanidinium, alkylhydroxy, alkoxyhydroxy, alkoxyamine, alkoxy-substituted amine, and azido groups, COOH, alkyl-COOH, $CONH_2$ and alkyl-$CONH_2$ with the other of $R_3$ and $R_6$ selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; and Y is selected from the group consisting of C=O, CH—OH, S=O, and $SO_2$.

10. The composition according to claim 9 having two or more compounds having Formula X.

11. The composition according to claim 9, further including an additional antimicrobial agent.

12. The composition according to claim 9 where A is oxygen.

13. The composition according to claim 9 where A is oxygen and Y is carbonyl.

14. The composition according to claim 13 where at least one of $R_3$–$R_6$ is an alkoxyamine.

15. The composition according to claim 13 where two or more of $R_3$–$R_6$ are alkoxyamines.

16. The composition according to claim 13 wherein the compound is selected from the group consisting of 3,6-bis-N,N-diethylaminoxanthone, 3,6-bis-β-(N,N-diethylamino)ethoxyxanthone, 3,6-bis-γ-(N,N-diethylamino)propoxyxanthone, 3,6-bis-δ-(N,N-diethylamino)butoxyxanthone, 3,6-bis-ε-(N,N-diethylamino)amyloxyxanthone, 3,6-bis-ζ-(N,N-diethylamino)hexyloxyxanthone, 3,6-bis-η-(N,N-diethylamino)heptyloxyxanthone, 3,6-bis-θ-(N,N-diethylamino)octyloxyxanthone, 3,6-bis-ι-(N,N-diethylamino)nonyloxyxanthone, 3,6-bis-κ-(N,N-diethylamino)decyloxyxanthone, 4,5-bis-N,N-diethylaminoxanthone, 4,5-bis-γ-(N,N-diethylamino)propoxyxanthone, 4,5-bis-δ-(N,N-diethylamino)butoxyxanthone, 4,5-bis-ε-(N,N-diethylamino)amyloxyxanthone, 4,5-bis-ζ-(N,N-diethylamino)hexyloxyxanthone, 4,5-bis-η-(N,N-diethylamino)heptyloxy-xanthone, 4,5-bis-θ-(N,N-diethylamino)octyloxyxanthone, 4,5-bis-ι-(N,N-diethylamino)nonyloxyxanthone, and 4,5-bis-κ-(N,N-diethylamino)decyloxyxanthone.

17. A method for inhibiting the growth of a microbial pathogen, comprising:
providing a compound according to Formula X, or a composition comprising a compound according to Formula X where A is oxygen or sulfur; $R_1$–$R_2$, $R_4$–$R_5$, and $R_7$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; at least one of $R_3$ and $R_6$ is independently selected from the group consisting of amino, substituted amino, alkylamino, substituted alkyl amino, arylamino, amidinium, alkylamidinium, guanidinium, alkylguanidinium, alkylhydroxy, alkoxyhydroxy, alkoxyamine, alkoxy-substituted amine, and azido groups, COOH, alkyl-COOH, $CONH_2$ and alkyl-$CONH_2$ with the other of $R_3$ and $R_6$ selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether, nitro and O-linked and C-linked carbohydrates; and Y is selected from the group consisting of C=O, CH—OH, S=O, and $SO_2$; and contacting the pathogen with an effective amount of the compound or composition.

18. The method according to claim 17 where in the compound A is oxygen.

19. The method according to claim 17 where in the compound A is oxygen and Y is carbonyl.

20. The method according to 19 where at least one of the compound's $R_3$–$R_6$ is an alkoxyamine.

21. The method according to claim 19 where two or more of the compound's $R_3$–$R_6$ are alkoxyamines.

22. The method according to claim 19 where the compound is selected from the group consisting of 3,6-bis-N,N-diethylaminoxanthone, 3,6-bis-β-(N,N-diethylamino)ethoxyxanthone, 3,6-bis-γ-(N,N-diethylamino)propoxyxanthone, 3,6-bis-δ-(N,N-diethylamino)butoxyxanthone, 3,6-bis-ε-(N,N-diethylamino)amyloxyxanthone, 3,6-bis-ζ-(N,N-diethylamino)hexyloxyxanthone, 3,6-bis-η-(N,N-diethylamino)heptyloxyxanthone, 3,6-bis-θ-(N,N-diethylamino)octyloxyxanthone, 3,6-bis-ι-(N,N-diethylamino)nonyloxyxanthone, 3,6-bis-κ-(N,N-diethylamino)decyloxyxanthone, 4,5-bis-N,N-diethylaminoxanthone, 4,5-bis-δ-N,N-diethylamino)butoxyxanthone, 4,5-bis-ε-(N,N-diethylamino)amyloxyxanthone, 4,5-bis-ζ-(N,N-diethylamino)hexyloxyxanthone, 4,5-bis-η-(N,N-diethylamino)heptyloxy-xanthone, 4,5-bis-θ-(N,N-diethylamino)octyloxyxanthone, 4,5-bis-ι-(N,N-diethylamino)nonyloxyxanthone, and 4,5-bis-κ-(N,N-diethylamino)decyloxyxanthone.

23. The composition according to claim 13 where at least one of $R_3$–$R_6$ is dialkylaminoalkoxy.

24. The method according to claim 17 where at least one of $R_3$–$R_6$ is dialkylaminoalkoxy.

25. A compound according to Formula X

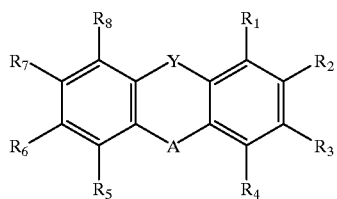

Formula X where A is oxygen; $R_1$–$R_2$, $R_4$–$R_5$, and $R_7$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether and nitro groups and O-linked and C-linked carbohydrates; at least one of $R_3$ and $R_6$ is dialkylaminoalkoxy with the other R group, if any, selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether and nitro groups and O-linked and C-linked carbohydrates; and Y is carbonyl.

26. A compound according to Formula X

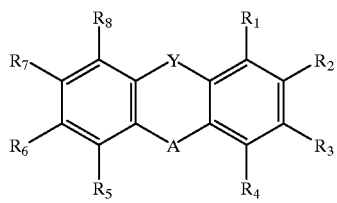

Formula X where A is oxygen; $R_1$–$R_2$, $R_4$–$R_5$, and $R_7$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether and nitro groups and O-linked and C-linked carbohydrates; $R_3$ and $R_6$ are dialkylaminoalkoxy; and Y is carbonyl.

27. A compound selected from the group consisting 3,6-bis-N,N-diethylaminoxanthone, 3,6-bis-β-(N,N-diethylamino)ethoxyxanthone, 3,6-bis-γ-(N,N-diethylamino)propoxyxanthone, 3,6-bis-δ-(N,N-diethylamino)butoxyxanthone, 3,6-bis-ε-(N,N-diethylamino)amyloxyxanthone, 3,6-bis-ζ-(N,N-diethylamino)hexyloxy-xanthone, 3,6-bis-η-(N,N-diethylamino)heptyloxyxanthone, 3,6-bis-θ-(N,N-diethylamino)octyloxyxanthone, 3,6-bis-ι-(N,N-diethylamino)nonyloxyxanthone, 3,6-bis-κ-(N,N-diethylamino)decyloxyxanthone, 4,5-bis-N,N-diethylaminoxanthone, 4,5-bis-γ-(N,N-diethylamino)propoxyxanthone, 4,5-bis-δ-(N,N-diethylamino)butoxyxanthone, 4,5-bis-ε-(N,N-diethylamino)amyloxyxanthone, 4,5-bis-ζ-(N,N-diethylamino)hexyloxyxanthone, 4,5-bis-η-(N,N-diethylamino)heptyloxy-xanthone, 4,5-bis-θ-(N,N-diethylamino)octyloxyxanthone, 4,5-bis-ι-(N,N-diethylamino)nonyloxyxanthone, and 4,5-bis-κ-(N,N-diethylamino)decyloxyxanthone.

28. The compound 3,6-bis-N,N-diethylaminoxanthone.

29. A composition comprising a pharmaceutical carrier and at least two compounds having Formula X

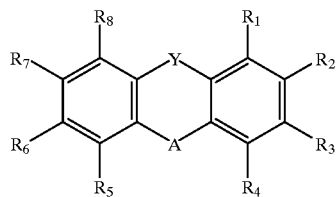

Formula X where A is oxygen or sulfur; $R_1$–$R_8$ are independently selected from the group consisting of H, OH, halogen, aryl, arylamine, alkyl, alkene, substituted alkyl, alkylthio, alkoxy, substituted alkoxy, cycloaminoalkoxy, substituted alkylthio, amino, amido, ester, ether and nitro groups and O-linked and C-linked carbohydrates; and Y is selected from the group consisting of C=O, CH—OH, S=O, and $SO_2$.

* * * * *